US006672585B2

(12) United States Patent
Nishida et al.

(10) Patent No.: US 6,672,585 B2
(45) Date of Patent: Jan. 6, 2004

(54) APPARATUS FOR STACKING SHEET MEMBERS, APPARATUS FOR MEASURING DIMENSIONS OF SHEET MEMBERS, AND APPARATUS FOR AND METHOD OF MARKING SHEET MEMBERS

(75) Inventors: Hiroyuki Nishida, Fujinomiya (JP); Masayuki Nakagiri, Fujinomiya (JP); Keisuke Endo, Fujinomiya (JP); Hideyuki Uezono, Fujinomiya (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 158 days.

(21) Appl. No.: 09/871,729

(22) Filed: Jun. 4, 2001

(65) Prior Publication Data
US 2001/0048192 A1 Dec. 6, 2001

(30) Foreign Application Priority Data

| Jun. 2, 2000 | (JP) | 2000-166600 |
| Jun. 7, 2000 | (JP) | 2000-171165 |
| Jun. 22, 2000 | (JP) | 2000-188309 |

(51) Int. Cl.[7] .............................................. B65H 31/00
(52) U.S. Cl. .................. 271/211; 414/793.4; 414/794.3
(58) Field of Search ................. 271/211, 213; 414/793.4, 794.3, 676

(56) References Cited

U.S. PATENT DOCUMENTS

| 2,675,928 | A | * | 4/1954 | Slater | 414/792.2 |
| 3,028,979 | A | * | 4/1962 | Zachow | 414/793.4 |
| 3,688,920 | A | * | 9/1972 | Frish | 414/790 |
| 3,756,427 | A | * | 9/1973 | Arnemann | 414/793.4 |
| 4,255,074 | A | * | 3/1981 | Meratti et al. | 414/792 |
| 4,395,038 | A | * | 7/1983 | Fitzpatrick et al. | 271/195 |
| 4,624,455 | A | * | 11/1986 | Radek et al. | 271/85 |
| 4,642,013 | A | * | 2/1987 | Mundus et al. | 414/790.7 |
| 4,708,564 | A | * | 11/1987 | Mylrea et al. | 414/789.1 |
| 4,898,511 | A | * | 2/1990 | Rossig et al. | 414/792.6 |
| 4,899,518 | A | * | 2/1990 | Beeman et al. | 53/439 |
| 4,902,195 | A | * | 2/1990 | Lucas | 414/799 |
| 5,051,058 | A | * | 9/1991 | Roth | 414/789.1 |
| 5,076,558 | A | * | 12/1991 | Bergeron et al. | 271/3.05 |
| 5,535,576 | A | * | 7/1996 | Walintschek | 53/501 |
| 6,394,443 | B1 | * | 5/2002 | Vedoy et al. | 271/3.14 |
| 2001/0006272 | A1 | * | 7/2001 | Gunschera et al. | 271/213 |
| 2003/0082043 | A1 | * | 5/2003 | Lunden | 414/789.5 |

FOREIGN PATENT DOCUMENTS

| JP | 4-9605 | 1/1992 | G01B/11/04 |
| JP | 4-209158 | 7/1992 | B65H/31/34 |
| JP | 5-52526 | 3/1993 | G01B/11/04 |
| JP | 6-147836 | 5/1994 | G01B/11/04 |

OTHER PUBLICATIONS

Patent Abstracts of Japan, 04009605 A, Jan. 14, 1992.
Patent Abstracts of Japan, 04209158 A, Jul. 30, 1992.
Patent Abstracts of Japan, 05052526 A, Mar. 2, 1993.
Patent Abstracts of Japan, 06147836 A, May 27, 1993.

* cited by examiner

Primary Examiner—Donald P. Walsh
Assistant Examiner—Joseph C Rodriguez
(74) Attorney, Agent, or Firm—Sughrue Mion, PLLC

(57) ABSTRACT

An apparatus for stacking a predetermined number of X-ray films has a sheet member holding device disposed above a stacking position for temporarily holding at least a first X-ray film, and an actuating device for displacing the sheet member holding device from the stacking position to drop the X-ray film held by the sheet member holding device into the stacking position. The apparatus is capable of stacking a plurality of X-ray films highly accurately and efficiently in the stacking position while avoiding damage to the X-ray films.

9 Claims, 22 Drawing Sheets

FIG. 8

| WAVELENGTH OF INFRARED LIGHT [nm] | POSSIBILITY OF FOGGING |
|---|---|
| 700~800 | YES |
| 800~900 | YES |
| 900~1000 | NO |

FIG. 21

| TYPE | EXPOSURE TIME ($\mu$s) | CURRENT (mA) |
|---|---|---|
| A | 2 | 20 |
| B | 10 | 20 |
| C | 20 | 20 |
| D | 10 | 100 |

APPARATUS FOR STACKING SHEET MEMBERS, APPARATUS FOR MEASURING DIMENSIONS OF SHEET MEMBERS, AND APPARATUS FOR AND METHOD OF MARKING SHEET MEMBERS

BAKCGROUND OF THE INVENTION

1. Field of the Invention

The present invention relates to an apparatus for stacking a predetermined number of sheet members that are successively charged via a feed system in a stacking position, an apparatus for measuring dimensions of sheet members, and an apparatus for and a method of marking sheet members.

2. Description of the Related Art

There have been used packaged products each comprising a stack of sheet members, e.g., sheet-like photosensitive members such as X-ray films, which are packaged by a package film as a light shielding member. For producing such packaged products, it is customary to stack a predetermined number of sheet-like photosensitive members with a stacking device before the sheet-like photosensitive members are delivered to a next process such as a packaging process or the like.

In the stacking device, sheet-like photosensitive members are successively supplied to a stacking position by a feed system such as a belt conveyor or the like, and then successively dropped onto an lining cardboard, a product tray, or a stacking bottom plate. For example, Japanese laid-open patent publication No. 4-209158 discloses a sheet-like member stacking apparatus which has a sheet holding means for vertically stacking and holding a plurality of sheet-like members in a given stacking position, a sheet supply means for supplying sheet-like members substantially horizontally from a position near the stacking position to a position over the stacking position, and dropping the sheet-like members to the stacking position, and a suction means for pulling downwardly a rear end of the sheet supply means.

The suction means generates an air flow for lowering the rear end of a sheet-like member that is dropped to the stacking position by the sheet supply means. Since the air flow quickly lowers the rear end of the sheet-like member that is dropped by the sheet supply means, a succeeding sheet-like member does not hit the preceding sheet-like member. Thus, successive sheet-like members can smoothly and efficiently be stacked in the stacking position.

With the conventional sheet-like member stacking apparatus, sheet members cannot be delivered or expelled to a front stopper for limiting front end positions thereof if the speed for stacking sheet members is set to a relatively low value. A first sheet member to be stacked is liable to impinge upon an lining cardboard, a product tray, or a stacking bottom plate that is placed in the stacking position, making it difficult to stack a desired number of sheet members stably in the stacking position and also tending to cause damage to the sheet members which suffer a reduction in product quality.

There are known apparatus including an electronic flash lamp and an optical sensor for measuring dimensions of a sheet member that is being fed. These known apparatus include an apparatus for applying light from an electronic flash lamp toward a sheet member, detecting light reflected from the sheet member with a camera, and detecting the position of ends of the sheet to measure dimensions of the sheet member (see Japanese laid-open patent publication No. 4-9605, for example) and an apparatus having an electronic flash lamp and a sensor that are disposed one on each side of a sheet member feed path, the sensor detecting a position where light from the electronic flash lamp is blocked by a sheet member to measure dimensions of the sheet member (see Japanese laid-open patent publications Nos. 5-52526 and 6-147836, for example).

There has been a demand for the measurement of dimensions of a sheet-like photosensitive member with an apparatus having an electronic flash lamp and an optical sensor as described above. One problem with the apparatus used for measuring dimensions of a sheet-like photosensitive member is that when light from the electronic flash lamp is applied to the sheet-like photosensitive member, the sheet-like photosensitive member is apt to be fogged. Consequently, it has been difficult to use the apparatus for the purpose of measuring dimensions of a sheet-like photosensitive member.

Sheet-like photosensitive members are marked by a marking device with a latent image of a manufacturing lot number representing manufacturing information such as a processed sequence and an ISO sensitivity value representing the sensitivity of the sheet-like photosensitive member. The marked information is turned into a visible image when the sheet-like photosensitive member, such as an X-ray film, is processed by a developing process. The marked information becomes effective for the user if the X-ray film is defective, for example.

The marking device uses LEDs as light sources for emitting light with several colors as a means for marking desired letters or the like on X-ray films. For example, green light emitted from a green LED and red light emitted from a red LED are mixed into yellow light, which is applied to an X-ray film to mark the X-ray film with desired letters or the like. Each of the LEDs is connected to an LED driver for energizing the LED for light emission.

Since the marking device uses a plurality of LEDs, it also requires as many LED drivers as the number of LEDs, and hence necessarily becomes large in size. In addition, the marking device needs a complex control system for the LED drivers. The complex control system cannot easily be maintained and managed, and tends to increase the equipment cost of the marking device.

SUMMARY OF THE INVENTION

It is a general object of the present invention to provide an apparatus for smoothly and reliably stacking sheet members in a stacking position while effectively preventing the sheet members from being damaged.

A major object of the present invention is to provide an apparatus for measuring dimensions of sheet members without allowing the sheet members to be fogged.

Another major object of the present invention is to provide an apparatus for and a method of marking sheet members with desired letters or the like with only white LEDs, so that the cost of equipment used is reduced.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 8 is a table showing the relationship between wavelengths of infrared radiation and the fogging of a photographic film;

FIG. 21 is a table showing exposure conditions for the types of X-ray films that are stored in a memory of the controller.

DESCRIPTION OF THE PREFERRED EMBODIMENTS

Figure 1:
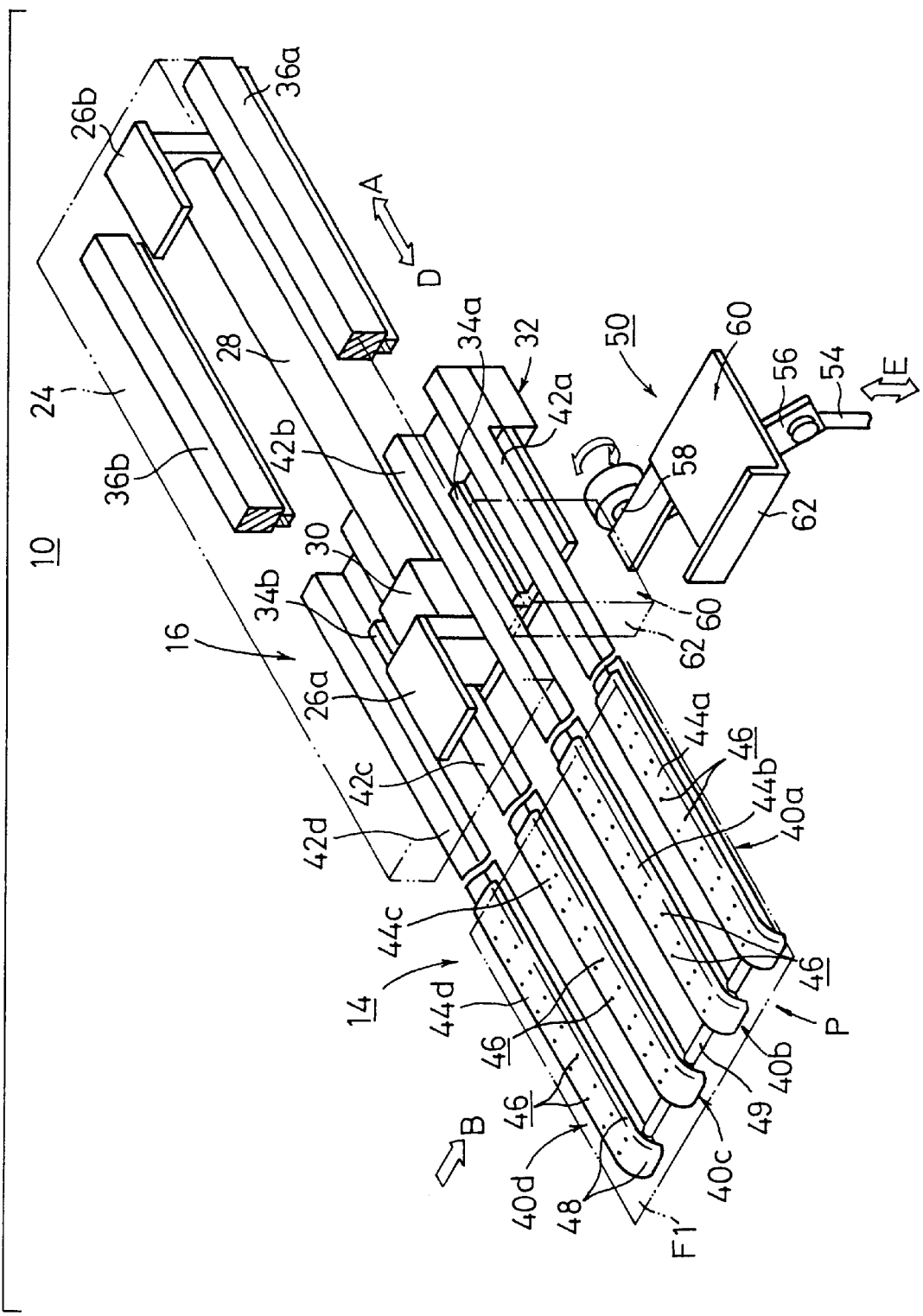
FIG. 1 is a fragmentary perspective view of an apparatus for stacking sheet members according to a first embodiment of the present invention.
Figure 2:
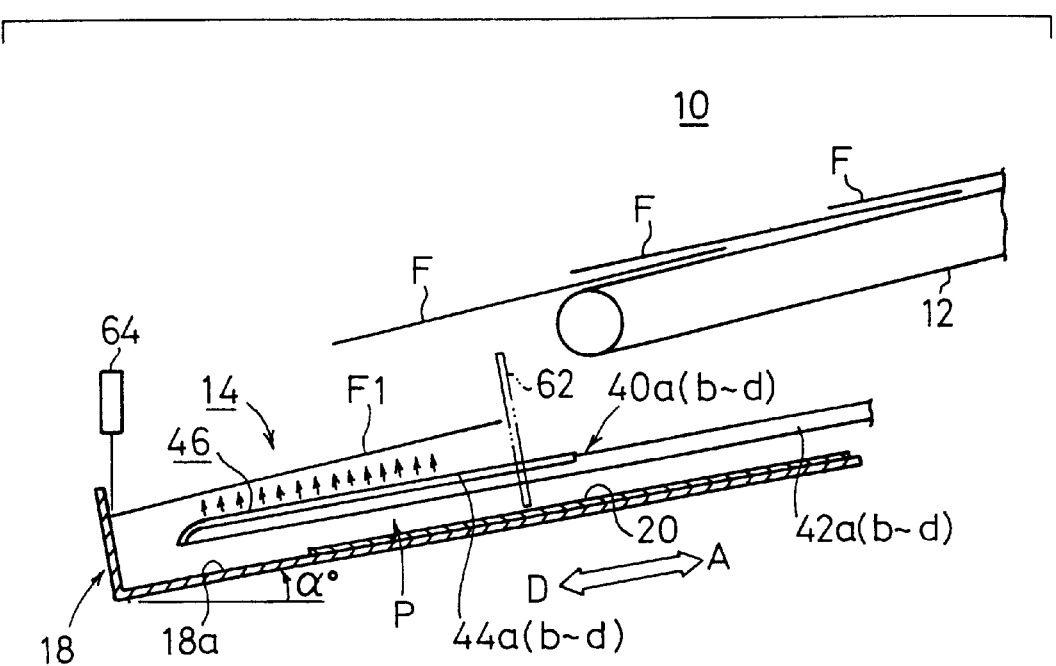
FIG. 2 is a side elevational view of the stacking apparatus.

FIG. 1 shows in fragmentary perspective an apparatus 10 for stacking sheet members according to a first embodiment of the present invention, and FIG. 2 shows in side elevation the stacking apparatus 10.

As shown in FIGS. 1 and 2, the stacking apparatus 10 has a function to stack a predetermined number of sheet members, such as X-ray films F, successively charged by a conveyor (feed system) 12 in a stacking position P. The stacking apparatus 10 comprises a sheet member holding means 14 disposed above the stacking position P for temporarily holding at least a first X-ray film F1 that is charged, and an actuating means 16 for displacing the sheet member holding means 14 from above the stacking position P in the direction indicated by the arrow A to drop the X-ray film F1 held by the sheet member holding means 14 into the stacking position P.

Figure 3:
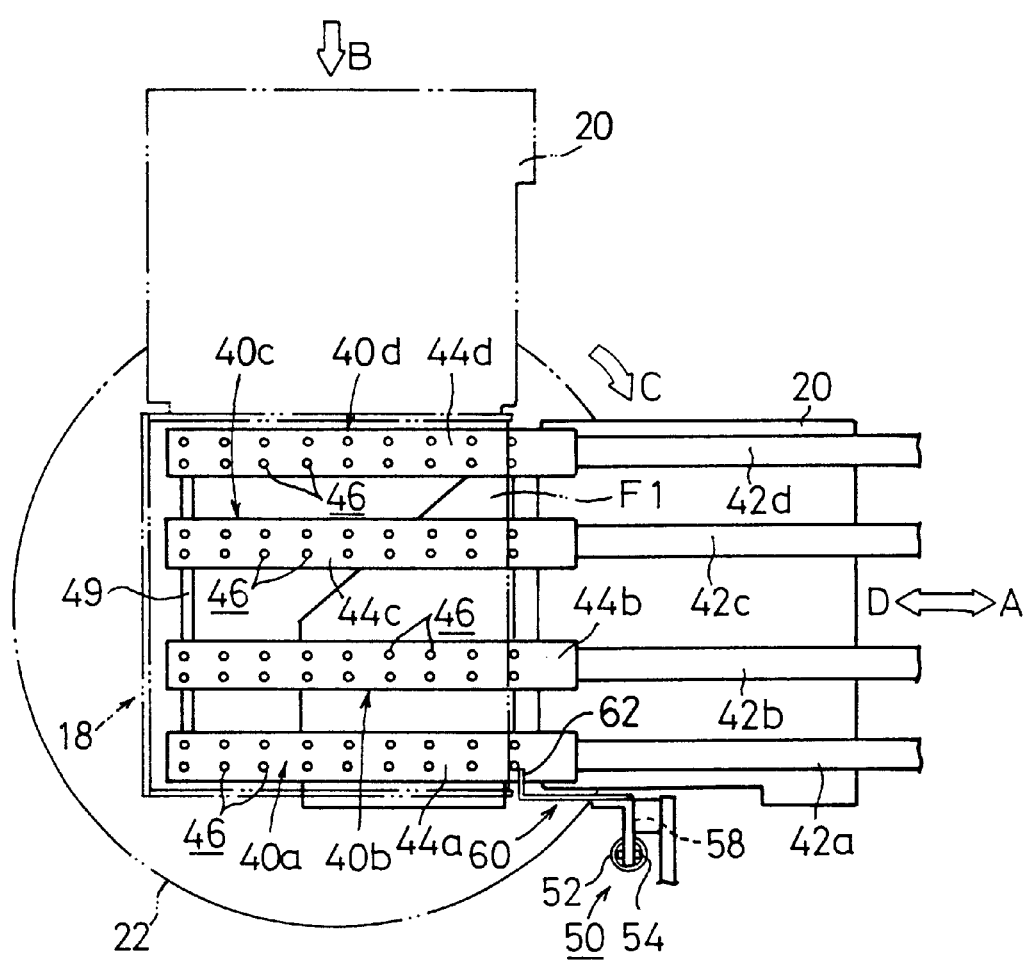
FIG. 3 is a plan view of the stacking apparatus.

As shown in FIGS. 2 and 3, a stacking frame 18 is disposed around the stacking position P. The stacking frame 18 is tilted at α°, e.g., 20°, from the horizontal plane. A turntable 22 is disposed in the stacking position P for holding an lining cardboard 20 that has been fed in the direction indicated by the arrow B in FIG. 3 and turning the lining cardboard 20 by 90° in the direction indicated by the arrow C. The lining cardboard 20 has a portion placed on a stacking bottom plate 18a of the stacking frame 18.

Figure 4:
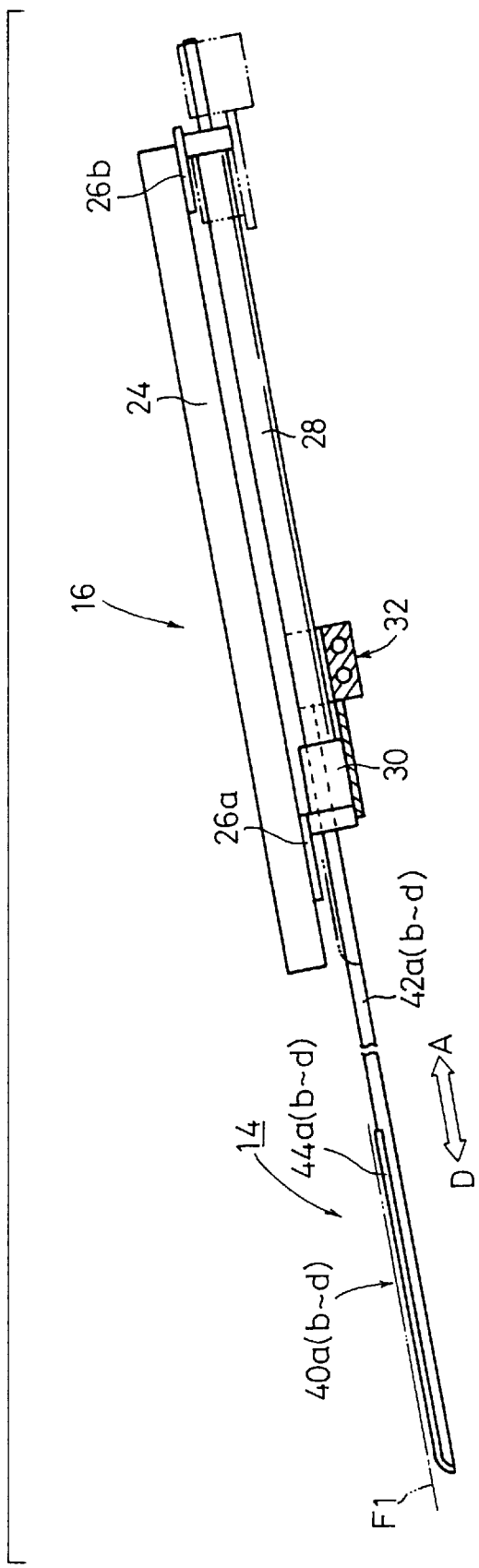
FIG. 4 is a side elevational view of an actuating means and a sheet member holding means of the stacking apparatus.

As shown in FIGS. 1 and 4, the actuating means 16 has a base 24 extending in the directions indicated by the arrows A, D, and two support members 26a, 26b spaced from each other by a given distance are fixed to the bottom surface of the base 24. On the base 24 between the support members 26a, 26b, there is supported a rodless cylinder 30 that is movable back and forth along a guide bar 28, with a movable base 32 fixed to the rodless cylinder 30. Linear guides 34a, 34b are mounted on the movable base 32, and guide rails 36a, 36b are mounted on the bottom surface of the base 24 in movable engagement with the linear guides 34a, 34b and extend in the directions indicated by the arrows A, D.

The sheet member holding means 14 has a plurality of, e.g., four temporary receiver rods 40a, 40b, 40c, 40d, extending in the direction in which the X-ray film F (F1) is charged, i.e., in the direction indicated by the arrow D. The temporary receiver rods 40a, 40b, 40c, 40d have respective pipes 42a, 42b, 42c, 42d of rectangular cross section which are fixed to the movable base 32 in sandwiching relation to the linear guides 34a, 34b and the rodless cylinder 30.

Plates 44a, 44b, 44c, 44d are fixed by welding or the like to respective upper surfaces of distal ends of the pipes 42a, 42b, 42c, 42d which project from the movable base 32 in the direction indicated by the arrow D. The plates 44a, 44b, 44c, 44d face the X-ray film F (F1). The plates 44a, 44b, 44c, 44d have NEDOX coatings on their surfaces which are made of electroless nickel precipitated in a granular form, impregnated with polytetrafluoroethylene (PTFE), and thermally treated, for a reduced coefficient of friction.

Each of the plates 44a, 44b, 44c, 44d has a plurality of air ejection holes 46 that are open toward the X-ray film F1 that is charged. The air injection holes 46 are connected through the pipes 42a, 42b, 42c, 42d to an air source, not shown, such as an air blower. Specifically, if the X-ray film F1 has a size of 430 mm×354 mm, then the plates 44a, 44b, 44c, 44d have a total of 110 air injection holes 46 each having a diameter of 2 mm. Each of the plates 44a, 44b, 44c, 44d has round edges 48 on their opposite sides and distal ends. The pipes 42a, 42b, 42c, 42d have distal ends interconnected together by a joint bar 49 for keeping the pipes 42a, 42b, 42c, 42d at the same height.

As shown in FIGS. 1 and 3, the stacking apparatus 10 has a variable stopper means 50 for engaging and releasing the X-ray film F1 from the sheet member holding means 14 when the sheet member holding means 14 that is holding the X-ray film F1 is moved in the direction indicated by the arrow A. The stopper means 50 has a rod 54 vertically movable in the directions indicated by the arrow E by a cylinder (actuator) 52, and a rotatable shaft 58 coupled to an upper end of the rod 54 by a cam plate 56. A plate-like pulling guide 60 is fixed at one end thereof to the rotatable shaft 58, and has a guide 62 on a distal end thereof in the direction indicated by the arrow D, the guide 62 being bent toward the X-ray film F (F1).

As shown in FIG. 2, a sheet member sensor 64 is positioned above the distal end of the stacking frame 18 for detecting the first X-ray film F1 when it is held by the sheet member holding means 14.

Operation of the stacking apparatus 10 thus constructed will be described below.

As shown in FIG. 2, the conveyor 12 feeds X-ray films F in a partly overlapping fashion successively in the direction indicated by the arrow D. The temporary receiver rods 40a, 40b, 40c, 40d of the sheet holding means 14 are disposed above the stacking position P. The temporary receiver rods 40a, 40b, 40c, 40d eject air from the air ejection holes 46 that are defined in the plates 44a, 44b, 44c, 44d and open upwardly.

The first X-ray film F1 is charged from the conveyor 12 into the stacking position P. The charged X-ray film F1 is temporarily held by the plates 44a, 44b, 44c, 44d on the temporary receiver rods 40a, 40b, 40c, 40d above the stacking position P. The sheet member sensor 64 disposed above the distal end of the stacking frame 18 detects when the X-ray film F1 is placed on the plates 44a, 44b, 44c, 44d.

Based on a detected signal from the sheet member sensor 64, the rodless cylinder 30 of the actuating means 16 is actuated, and the stopper means 50 is actuated prior to the actuation of the rodless cylinder 30, placing the pulling guide 60 in an upright position as indicated by the two-dot-and-dash lines in FIG. 1. When the rodless cylinder 30 moves along the guide bar 28 in the direction indicated by the arrow A, the movable base 32 fixed to the rodless cylinder 30 moves in unison with the temporary receiver rods 40a, 40b, 40c, 40d in the direction indicated by the arrow A, bringing the temporary receiver rods 40a, 40b, 40c, 40d away from the stacking position P.

At this time, as shown in FIG. 3, the pulling guide 60 of the stopper means 50 is held in the upright position, with the guide 62 projecting toward the X-ray film F1. Therefore, when the temporary receiver rods 40a, 40b, 40c, 40d move in the direction indicated by the arrow A, the X-ray film F1 engages the guide 62 and is held above the stacking position P, so that the temporary receiver rods 40a, 40b, 40c, 40d are reliably released from the X-ray film F1.

Figure 5:
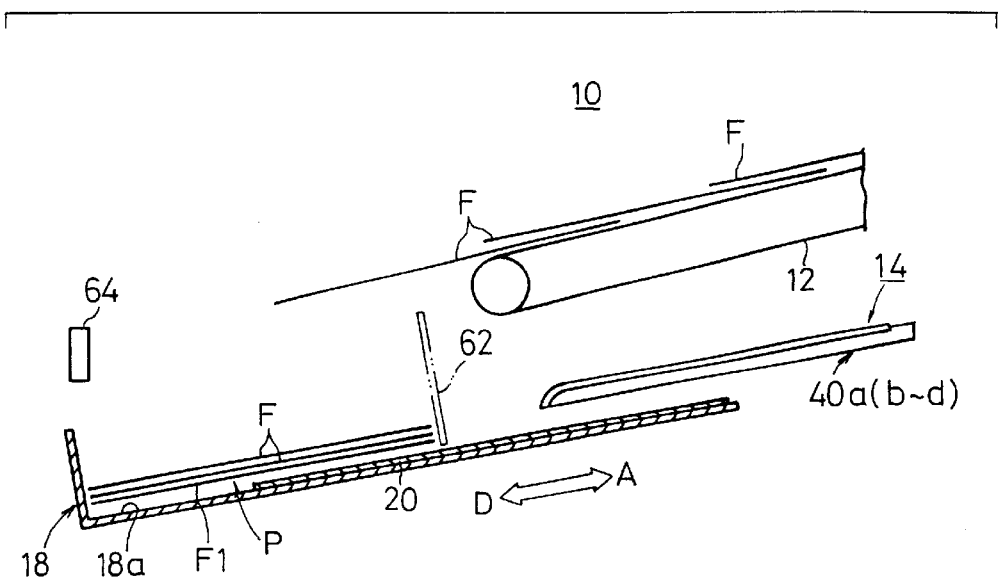
FIG. 5 is a side elevational view showing the manner in which the stacking apparatus operates to stack sheet members in a stacking position.

As shown in FIG. 5, the first X-ray film F1 is dropped onto the stacking bottom plate 18a and the lining cardboard 20 in the stacking frame 18. Thereafter, second and following X-ray films F are successively supplied from the conveyor 12 and stacked onto the first X-ray film F1. When a desired number of X-ray films F have been stacked in the stacking frame 18, the stacked X-ray films F and the lining cardboard 20 are delivered to a next process, and a new lining cardboard 20 is brought into the stacking position P.

Then, the rodless cylinder 30 of the actuating means 16 moves along the guide bar 28 in the direction indicated by the arrow D until the temporary receiver rods 40a, 40b, 40c, 40d are placed above the stacking position P. After the previous X-ray films F have been stacked, the pulling guide 60 has been retracted from the stopping position as indicated by the solid lines in FIG. 1. Then, the pulling guide 60 is angularly moved from the solid-line position to the two-dot-and-dash-line position at a predetermined time.

In the first embodiment, as described above, the first X-ray film F1 that is directly placed on the stacking bottom plate 18a and the lining cardboard 20 in the stacking position P is temporarily held by the sheet member holding means 14 that is placed above the stacking position P. Then, the sheet member holding means 14 moves in the direction indicated by the arrow A, allowing the X-ray film F1 held by the sheet member holding means 14 to drop into the stacking position P.

Therefore, the X-ray film F1 does not impinge upon the stacking bottom plate 18a and the lining cardboard 20 which have a coefficient of friction greater than the coefficient of friction of X-ray films. The first X-ray film F1 is thus free from a stacking failure due to undue friction and a quality failure such as damage due to impingement in the stacking position P, which would otherwise occur if the X-ray film F would directly drop from the conveyor 12 into the stacking position P. The X-ray film F1 can accurately and smoothly be placed in a desired position in the stacking frame 18.

The surfaces of the plates 44a, 44b, 44c, 44d of the sheet holding means 14 have NEDOX coatings for effectively avoiding adverse effects due to friction between the X-ray film F1 and the plates 44a, 44b, 44c, 44d.

Air is ejected from the air ejection holes 46 defined in the plates 44a, 44b, 44c, 44d toward the X-ray film F1. The ejected air virtually reduces the coefficient of friction between the X-ray film F1 and the plates 44a, 44b, 44c, 44d to a low level ranging from 0.2 to 0.03. Therefore, the X-ray film F1 can move smoothly on the plates 44a, 44b, 44c, 44d without being damaged thereby. The round edges 48 of the plates 44a, 44b, 44c, 44d are effective to prevent the X-ray film F1 from being caught by the plates 44a, 44b, 44c, 44d.

When the temporary receiver rods 40a, 40b, 40c, 40d which are holding the X-ray film F1 are moved in the direction indicated by the arrow A, the guide 62 of the stopper means 50 engages the X-ray film F1, allowing the X-ray film F1 to drop reliably and smoothly into the stacking position P.

In the first embodiment, the sheet member sensor 64 detects when the X-ray film F1 is placed on the temporary receiver rods 40a, 40b, 40c, 40d. Therefore, the X-ray film F1 can be dropped quickly and reliably into the stacking position P, and second and following X-ray films F can reliably be stacked onto the X-ray film F1. As a result, the entire stacking process can easily be made highly efficient.

In the first embodiment, after the first X-ray film F1 is held by the sheet member holding means 14, the sheet member holding means 14 is moved in the direction indicated by the arrow A. However, the sheet member holding means 14 may be moved in the direction indicated by the arrow A after one or more X-ray films F have been stacked on the first X-ray film F1.

Figure 6:
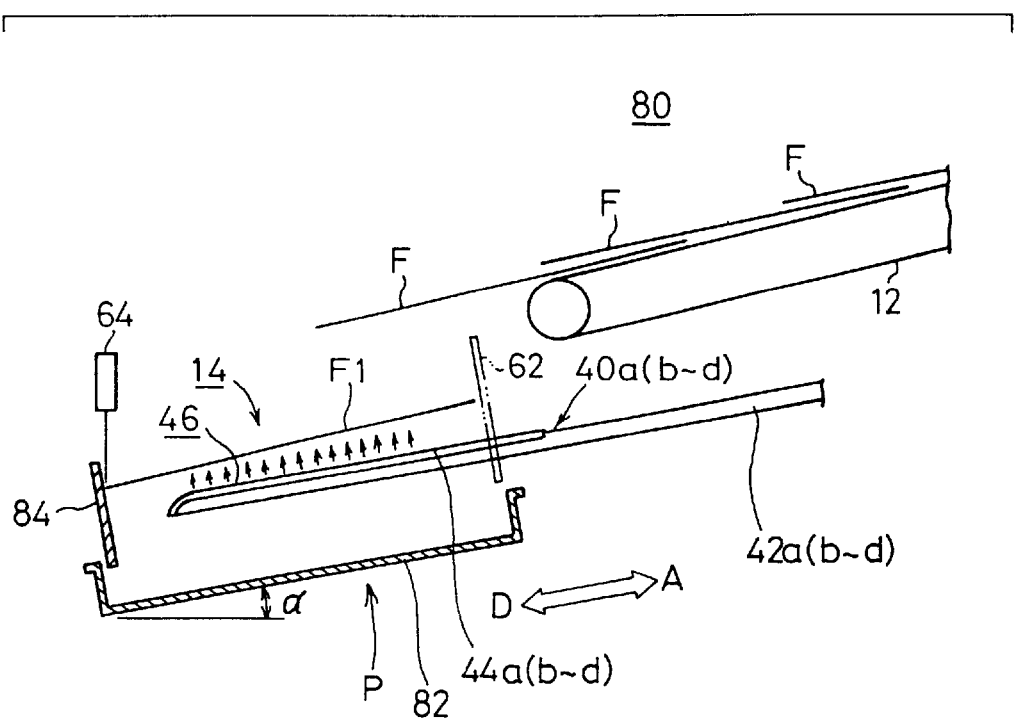
FIG. 6 is a side elevational view of an apparatus for stacking sheet members according to a second embodiment of the present invention.

FIG. 6 shows in side elevation an apparatus 80 for stacking sheet members according to a second embodiment of the present invention. Those parts of the stacking apparatus 80 which are identical to those of the stacking apparatus 10 according to the first embodiment are denoted by identical reference characters, and will not be described in detail below.

In the stacking apparatus 80, a product tray 82 is disposed in the stacking position P, and a stacking frame 84 is disposed above the product tray 82. The product tray 84 is tilted at α°, e.g., 20°, from the horizontal plane. In the second embodiment, the product tray 82 serves as a substitute for the lining cardboard 20 used in the first embodiment.

The first X-ray film F1 is directly placed in the product tray 82 in the stacking position P, and temporarily held by the sheet member holding means 14 that is placed above the stacking position P. Then, the sheet member holding means 14 is moved in the direction indicated by the arrow A, allowing the X-ray film F1 held by the sheet member holding means 14 to drop into the stacking position P.

Therefore, the X-ray film F1 does not impinge upon the product tray 82 which has a coefficient of friction greater than the coefficient of friction of X-ray films. The first X-ray film F1 is thus free from a stacking failure due to undue friction and a quality failure such as damage due to impingement in the stacking position P, which would otherwise occur if the X-ray film F would directly drop from the conveyor 12 into the stacking position P. The X-ray film F1 can accurately and smoothly be placed in a desired position in the stacking frame 18.

In the first and second embodiments, the X-ray film F (F1) is used as a sheet member. However, the principles of the present invention are also applicable to any of various other types of sheet members.

Figure 7:
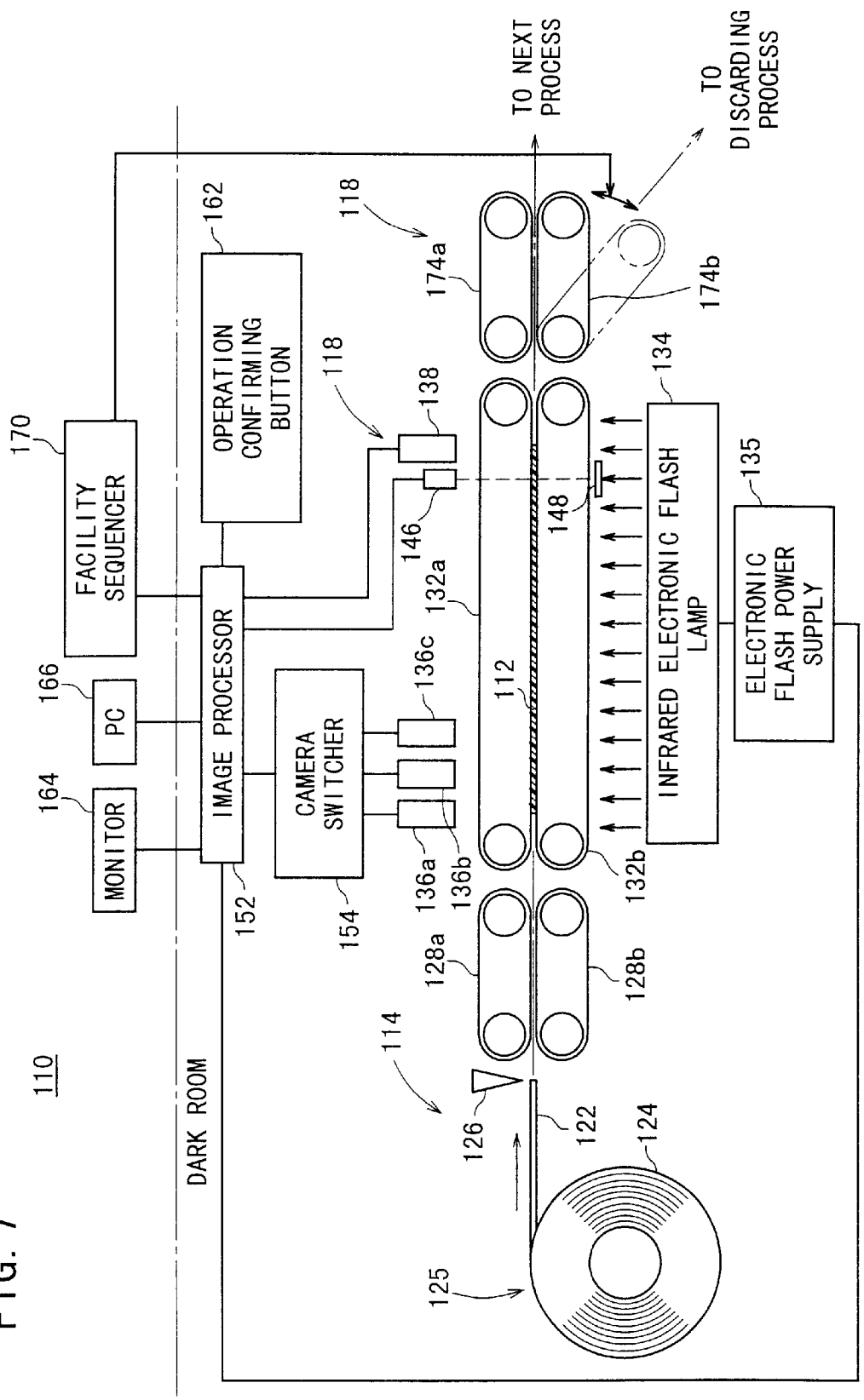
FIG. 7 is a block diagram of an apparatus for measuring dimensions of sheet members according to a third embodiment of the present invention.

FIG. 7 shows in block form an apparatus 110 for measuring dimensions of sheet members according to a third embodiment of the present invention.

The measuring apparatus 110 comprises a sheet supply device 114 for supplying a sheet-like photosensitive member 112 as a sheet member, a dimension measuring device 116 for measuring dimensions of the sheet-like photosensitive member 112 while feeding the sheet-like photosensitive member 112, and a defect rejecting device 118 for rejecting any sheet-like photosensitive member 112 whose dimensions are not according to desired standards. The sheet supply device 114, the dimension measuring device 116, and the defect rejecting device 118 are housed in a dark chamber.

The sheet supply device 114 comprises an unreeling unit 125 for unreeling a photosensitive member 122 from a roll 124 thereof, a cutting unit 126 for cutting off the photosensitive member 122 into a sheet-like photosensitive member 112, and a pair of front belt conveyors 128a, 128b for vertically gripping the produced sheet-like photosensitive member 112 and delivering the sheet-like photosensitive member 112 to the dimension measuring device 116.

The dimension measuring device 116 has a pair of belt conveyors 132a, 132b for vertically gripping the produced sheet-like photosensitive member 112 and delivering the sheet-like photosensitive member 112. An electronic flash lamp (light source) 134 for emitting infrared light for a given period of time only is disposed below the belt conveyors 132a, 132b. The electronic flash lamp 134 may be replaced with a matrix of infrared LEDs.

The electronic flash lamp 134 is energized by a voltage that is applied from an electronic flash power supply 135 according to a control signal from an image processor 152, described later on.

If the sheet-like photosensitive member 112 includes a photographic film, then the photographic film is prevented from being fogged because infrared light is applied from the electronic flash lamp 134. If the photographic film is an X-ray film (regular or imager film), particularly, then it is preferable to use infrared light in a wavelength range of 900 nm or higher, e.g., from 900 nm to 1000 nm, for eliminating any fogging possibility thereof almost entirely, as shown in FIG. 8.

The electronic flash lamp 134 which emits infrared light may be replaced with an electronic flash lamp which emits ultraviolet light that prevents the sheet-like photosensitive member 112 from being fogged.

Above the belt conveyors 132a, 132b, there are disposed inlet CCD cameras (photodetectors) 136a, 136b, 136c and an outlet CCD camera (photodetector) 138 for two-dimensionally detecting infrared light emitted from the electronic flash lamp 134.

The inlet CCD cameras 136a, 136b, 136c are disposed in an array along the direction in which the sheet-like photosensitive member 112 is fed, at an inlet side of the belt conveyors 132a, 132b. The outlet CCD camera 138 is disposed at an outlet side of the belt conveyors 132a, 132b. The inlet CCD cameras 136a, 136b, 136c and the outlet CCD camera 138 are oriented such that their optical axes are directed toward the feed path of the sheet-like photosensitive member 112.

The inlet CCD cameras 136a, 136b, 136c and the outlet CCD camera 138 may detect light reflected from the sheet-like photosensitive member 112.

Figure 9:
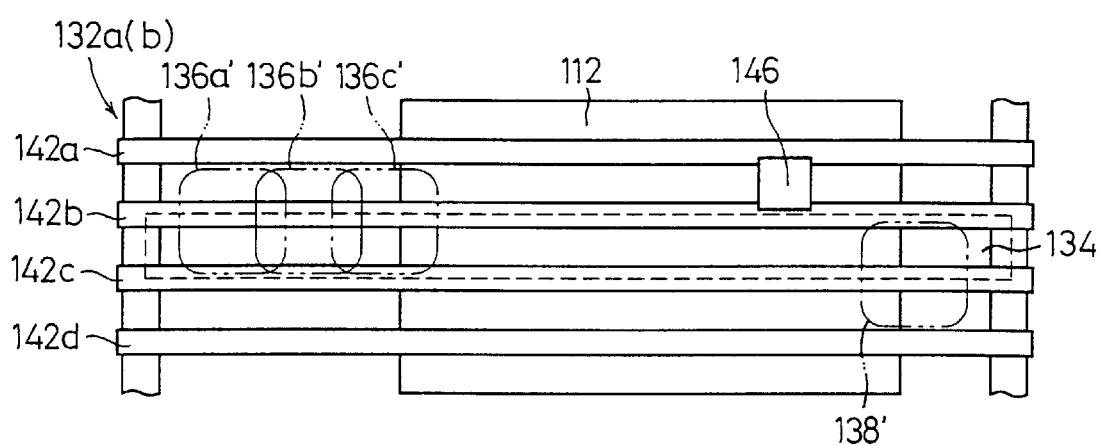
FIG. 9 is a plan view of a dimension measuring unit of the measuring apparatus shown in FIG. 7.

As shown in FIG. 9, the belt conveyors 132a, 132b have a plurality of, e.g., four, belts 142a, 142b, 142c, 142d spaced at given intervals. The electronic flash lamp 134 is positioned below the belts 142b, 142c, for example, such that the infrared light emitted from the electronic flash lamp 134 passes between the belts 142b, 142c upwardly through the feed path of the sheet-like photosensitive member 112.

In FIG. 9, the inlet CCD cameras 136a, 136b, 136c are installed in such a position that the area between the belts 142b, 142c is contained in lower portions of fields of vision 136a', 136b', 136c' of the inlet CCD cameras 136a, 136b, 136c, i.e., right portions of the fields of vision 136a', 136b', 136c' with respect to the direction in which the sheet-like photosensitive member 112 is fed, and the outlet CCD camera 138 is installed in such a position that the area between the belts 142b, 142c is contained in an upper portion of a field of vision 138' of the outlet CCD camera 138, i.e., a left portion of the field of vision 138' with respect to the direction in which the sheet-like photosensitive member 112 is fed. Thus, the infrared light from the electronic flash lamp 134 is detected by lower pixel areas of the inlet CCD cameras 136a, 136b, 136c, and an upper pixel area of the outlet CCD camera 138.

Each of the belts 142a, 142b, 142c, 142d has a width of about 25 mm, and adjacent two of the belts 142a, 142b, 142c, 142d are spaced from each other by a distance of about 35–19 mm. Each of the fields of vision 136a', 136b', 136c' of the inlet CCD cameras 136a, 136b, 136c and the field of vision 138' of the outlet CCD camera 138 has a size of about 100 mm×100 mm.

As shown in FIG. 7, a photosensor 146 as an end detecting means is disposed above the belt conveyors 132a, 132b upstream of the outlet CCD camera 138. The photosensor 146 comprises a reflective photosensor, for example, and emits light toward a reflecting plate 148 disposed beneath the belt conveyors 132a, 132b and detects light reflected from the reflecting plate 148. The photosensor 146 detects the position of a leading end of the sheet-like photosensitive member 112 based on whether it detects light reflected from the reflecting plate 148.

As shown in FIGS. 7 and 9, the photosensor 146 is disposed in a position to be able to emit and detect light through a gap between the belts 142a, 142b, for example, i.e., in a position where the reflecting plate 148 does not block the infrared light from the electronic flash lamp 134.

As shown in FIG. 7, the electronic flash power supply 135, the outlet CCD camera 138, and the photosensor 146 are electrically connected to the image processor 152 which serves as a data processor. The inlet CCD cameras 136a, 136b, 136c are electrically connected to the image processor 152 via a camera switcher 154.

When the image processor 152 confirms that the leading end of the sheet-like photosensitive member 112 has reached a position where it can be imaged by the outlet CCD camera 138 based on a detected signal from the photosensor 146, the image processor 152 enables the electronic flash power supply 135 to energize the electronic flash lamp 134. When the outlet CCD camera 138 and the inlet CCD cameras 136a, 136b, 136c detect the infrared light from the electronic flash lamp 134, the image processor 152 captures image data generated based on the infrared light from the outlet CCD camera 138 and the inlet CCD cameras 136a, 136b, 136c.

The inlet CCD cameras 136a, 136b, 136c are selected by the camera switcher 154 depending on the standard length L0 of the sheet-like photosensitive member 112 so as to be able to image the trailing end of the sheet-like photosensitive member 112.

Figure 10:
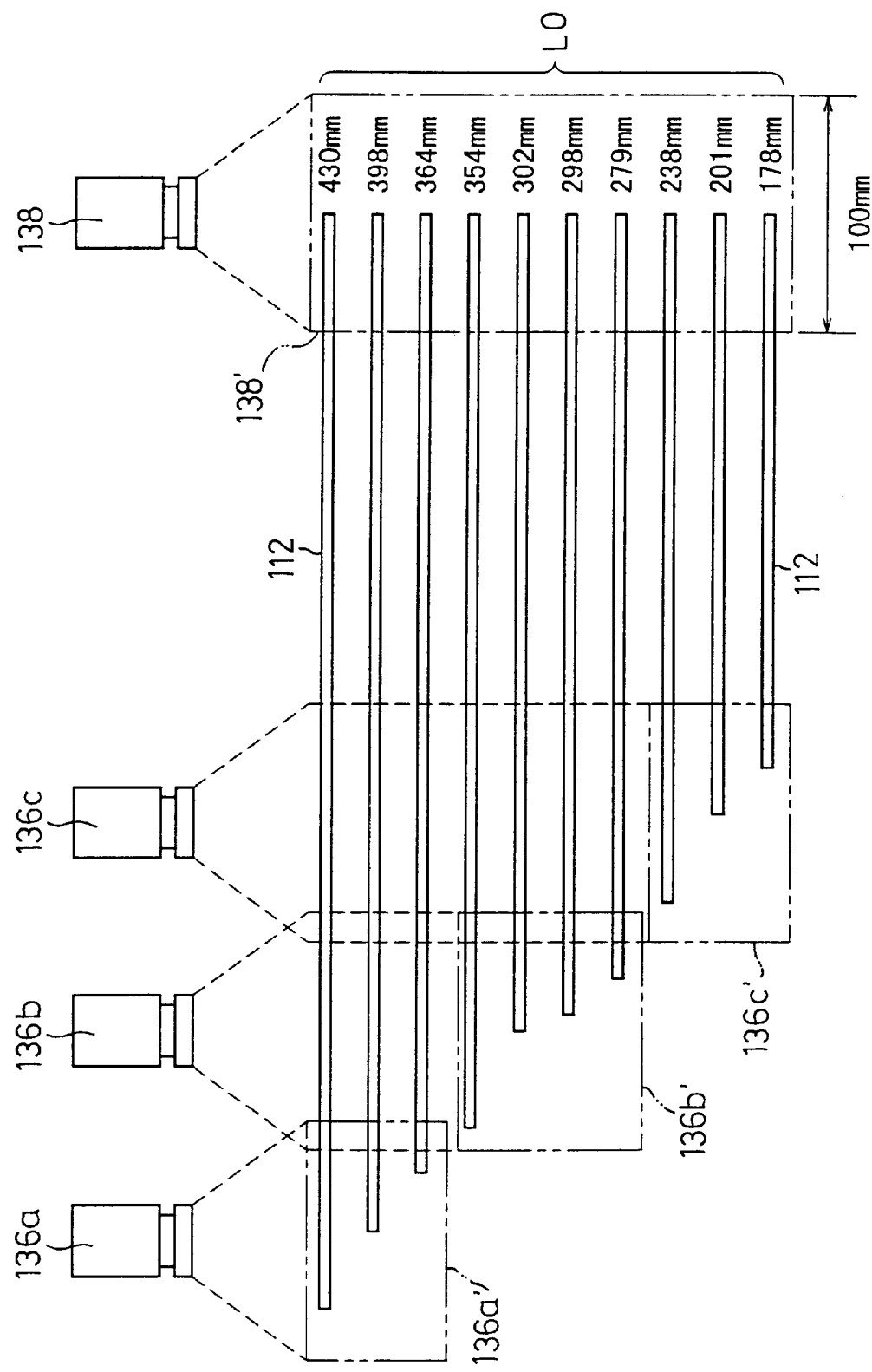
FIG. 10 is a view showing the relationship between standard lengths of sheet members and the positions of outlet and inlet CCD cameras.

For example, if the sheet-like photosensitive member 112 has a standard length L0 of 430 mm, 398 mm, or 364 mm, as shown in FIG. 10, then the left inlet CCD camera 136a is selected by the camera switcher 154. If the sheet-like photosensitive member 112 has a standard length L0 of 354 mm, 302 mm, 298 mm, or 279 mm, as shown in FIG. 10, then the middle inlet CCD camera 136b is selected by the camera switcher 154. If the sheet-like photosensitive member 112 has a standard length L0 of 238 mm, 201 mm, or 178 mm, as shown in FIG. 10, then the right inlet CCD camera 136c is selected by the camera switcher 154.

As shown in FIG. 7, the image processor 152 is electrically connected to an operation confirming button 162 disposed in the dark room, and a monitor 164 and a personal computer (PC) (threshold setting means) 166 that are disposed outside of the dark chamber. The monitor 164 displays information of an image produced by the outlet CCD camera 138 and the inlet CCD cameras 136a, 136b, 136c. The user can use the personal computer 166 to establish settings for the image processor 152.

The image processor 152 is also electrically connected to a facility sequencer 170 that is disposed outside of the dark chamber. The facility sequencer 170 serves to control the entire facility including the measuring apparatus 110.

The defect rejecting unit 118 disposed downstream of the dimension measuring unit 116 has rear belt conveyors 174a, 174b for feeding the sheet-like photosensitive member 112 that is delivered from the belt conveyors 132a, 132b.

The rear belt conveyors 174a, 174b can be opened and closed, i.e., can be moved relatively toward and away from each other, according to a control signal from the facility sequencer 170. When the rear belt conveyors 174a, 174b are closed, the sheet-like photosensitive member 112 is vertically gripped by the rear belt conveyors 174a, 174b and delivered to a next process. When the rear belt conveyors 174a, 174b are open, the sheet-like photosensitive member 112 is fed along the lower belt conveyor 174b to a discarding process.

Figure 11:
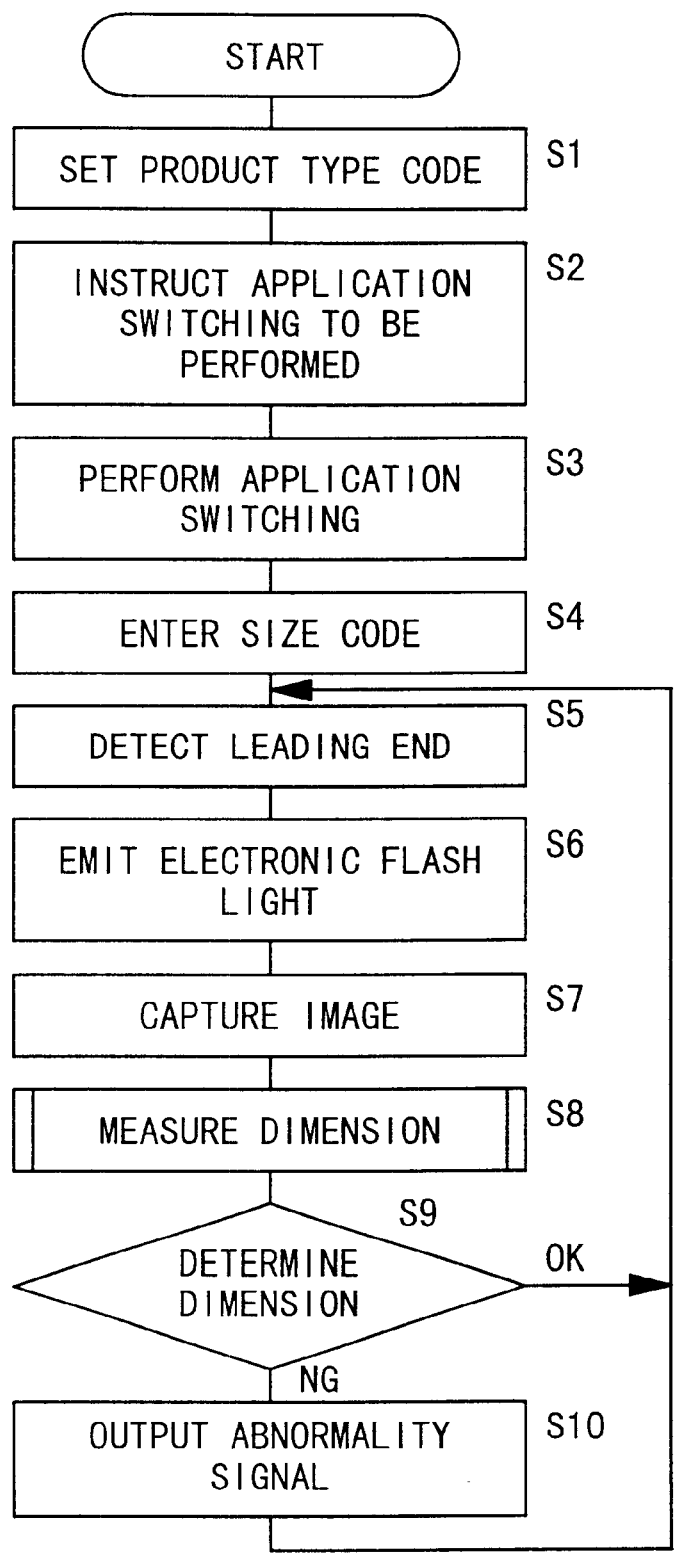
FIG. 11 is a flowchart of a processing sequence carried out by an image processor of the measuring apparatus.

A process carried out by the measuring apparatus 110, particularly, the image processor 152, will be described below with reference to FIGS. 11 and 12.

The image processor 152 is initially set in steps S1 through S4.

In step S1, the image processor 152 sets a product type code according to an instruction from the facility sequencer 170.

In step S2, the image processor 152 is supplied with a signal from the facility sequencer 170 for instructing an application switching process to be performed. In step S3, the image processor 152 effects the application switching process based on the signal from the facility sequencer 170.

In the application switching process, the image processor 152 sets a threshold α for use in a binary conversion process, described below.

The threshold α is set depending on the infrared transmittance as an optical property of the sheet-like photosensitive member 112. Specifically, the threshold α is set to a value which is capable of specifying the boundary position between the luminance level of infrared light that has reached the inlet CCD cameras 136a, 136b, 136c and the outlet CCD camera 138 directly from the electronic flash lamp 134 and the luminance level of infrared light that has reached the inlet CCD cameras 136a, 136b, 136c and the outlet CCD camera 138 through the sheet-like photosensitive member 112.

For example, the threshold α is set to one of values corresponding to changes of rate of the luminance level, e.g., one of increments of 5%, for example, in a range from 5% to 35%, for example.

In step S4, the image processor 152 is supplied with a size code from the facility sequencer 170. The supplied size code represents the standard length L0 of the sheet-like photosensitive member 112, and the image processor 152 selects one of the inlet CCD cameras 136a, 136b, 136c based on the standard length L0.

After the initial settings are finished in steps S1 through S4, the image processor 152 actuates the sheet supply device 114, the dimension measuring device 116, and the defect rejecting device 118 to start measuring dimensions of the sheet-like photosensitive member 112 based on an instruction from the facility sequencer 170.

In step S5, the image processor 152 confirms that the leading end of the sheet-like photosensitive member 112 has reached a given measuring position based on the detected signal from the photosensor 146. In step S6, the image processor 152 outputs a control signal to the electronic flash power supply 135. According to the control signal, the electronic flash power supply 135 applies a given voltage to the electronic flash lamp 134, which applies infrared light to the sheet-like photosensitive member 112.

The period of time for which the electronic flash lamp 134 is to be energized is determined depending on the accuracy that is required to measure dimensions of the sheet-like photosensitive member 112. For example, if an accuracy of 0.1 mm ($1 \times 10^{-4}$ m) is required and the sheet-like photosensitive member 112 is fed at a speed of 105 m/min. (1.75 m/s), then the period of time for which the electronic flash lamp 134 is to be energized is set to 57 ps or less, e.g., 50 ps.

In step S7, the image processor 152 captures image data based on an image, which represents the luminance of detected infrared light, generated by the inlet CCD cameras 136a, 136b, 136c and the outlet CCD camera 138, from these CCD cameras.

In step S8, the image processor 152 measures dimensions of the sheet-like photosensitive member 112 based on the captured image data. Details of the processing carried out in step S8 will be described later on.

In step S9, the image processor 152 determines whether the dimensions of the sheet-like photosensitive member 112 measured in step S8 satisfy predetermined reference values or not. If the dimensions of the sheet-like photosensitive member 112 measured in step S8 satisfy predetermined reference values (OK), then control goes back to step S5 to measure dimensions of a next sheet-like photosensitive member 112. If the dimensions of the sheet-like photosensitive member 112 measured in step S8 do not satisfy predetermined reference values (NG), then control goes to step S10.

In step S10, the image processor 152 outputs an abnormality signal to the facility sequencer 170. Then, the facility sequencer 170 applies a control signal to the rear belt conveyors 174a, 174b to open the rear belt conveyors 174a, 174b. When the rear belt conveyors 174a, 174b are opened according to the control signal, the sheet-like photosensitive member 112 that has been judged as defective is delivered to the discarding process. The sheet-like photosensitive member 112 that has not been judged as defective is delivered to a next process by the rear belt conveyors 174a, 174b that are closed.

After the processing in step S10, control returns to step S5 to measure dimensions of a next sheet-like photosensitive member 112.

Details of the processing carried out in step S8 will be described below.

Figure 12:
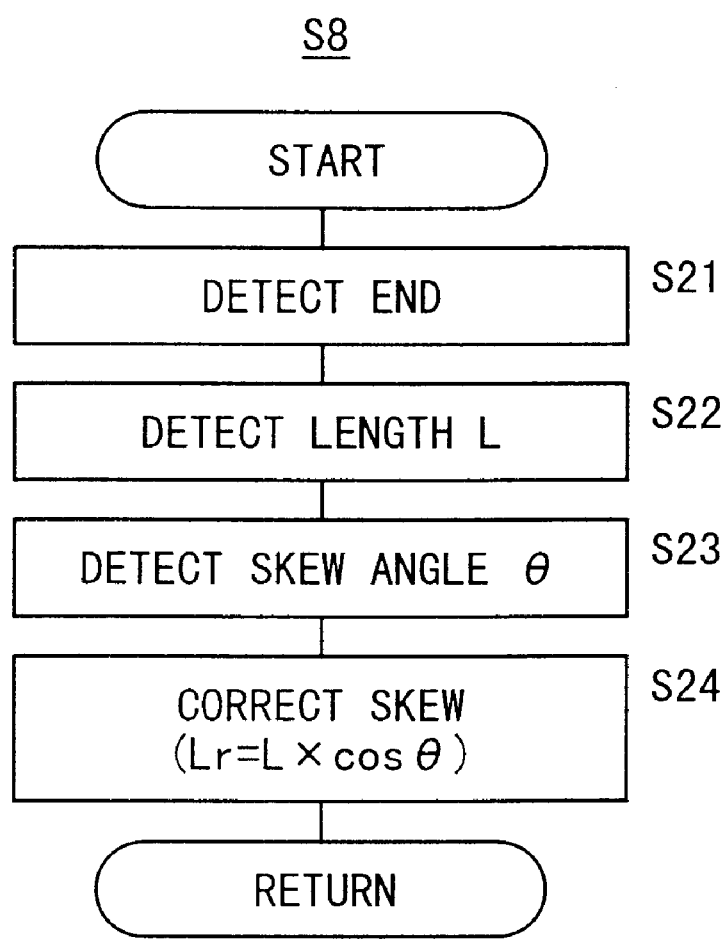
FIG. 12 is a flowchart of a subroutine of the processing sequence shown in FIG. 11.

FIG. 12 shows a subroutine representing the processing carried out in step S8. In step S21 (end detecting means), an end of the sheet-like photosensitive member 112 is detected.

Figure 13:
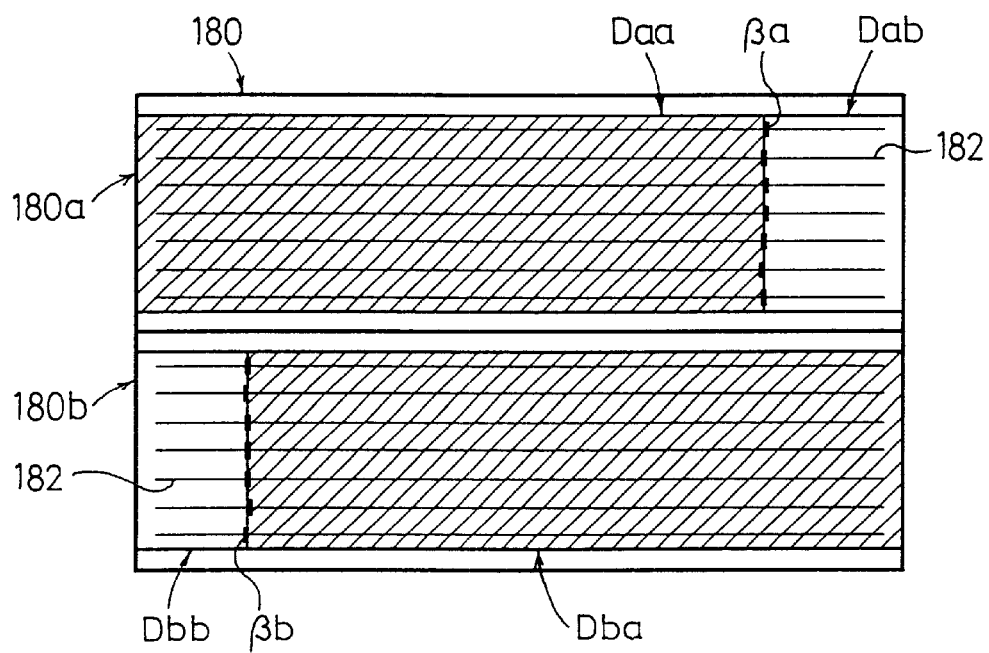
FIG. 13 is a diagram showing combined image data produced by the image processor.

Specifically, the image processor 152 generates combined image data 180 from the image data produced by the outlet CCD camera 138 and the image data produced by one of the inlet CCD cameras 136a, 136b, 136c, as shown in FIG. 13.

The combined image data 180 includes an upper area 180a comprising image data produced in an upper pixel range, in FIG. 9, of the outlet CCD camera 138, and a lower area 180b comprising image data produced in a lower pixel range, in FIG. 9, of one of the inlet CCD cameras 136a, 136b, 136c.

Seven line tools 182, for example, are established for each of the upper and lower areas 180a, 180b of the combined image data 180. Adjacent two of these line tools 182 are spaced about 5 mm from each other in terms of dimensions on the feed path of the sheet-like photosensitive member 112. These line tools 182 extend along the direction in which the sheet-like photosensitive member 112 is fed. Coordinates on the line tools 182 correspond to those on the feed path of the sheet-like photosensitive member 112.

The upper area 180a of the combined image data 180 includes data Daa of the luminance level of infrared light that has passed through a portion near the leading end of the sheet-like photosensitive member 112 and been detected by the outlet CCD camera 138, and data Dab of the luminance level of infrared light that has been reached directly from the electronic flash lamp 134 and detected by the outlet CCD camera 138.

The lower area 180b of the combined image data 180 includes data Dba of the luminance level of infrared light that has passed through a portion near the trailing end of the sheet-like photosensitive member 112 and been detected by the inlet CCD cameras 136a, 136b, 136c, and data Dbb of the luminance level of infrared light that has been reached directly from the electronic flash lamp 134 and detected by the inlet CCD cameras 136a, 136b, 136c.

Therefore, the combined image data 180 is constructed as data representing a distribution of luminance levels.

The end detecting means of the image processor 152 specifies coordinates βa, βb on the line tools 182 which correspond to the leading and trailing ends of the sheet-like photosensitive member 112, according to a binary conversion process based on the luminance levels in the combined image data 180 and the threshold α set in step S3.

Figure 14:
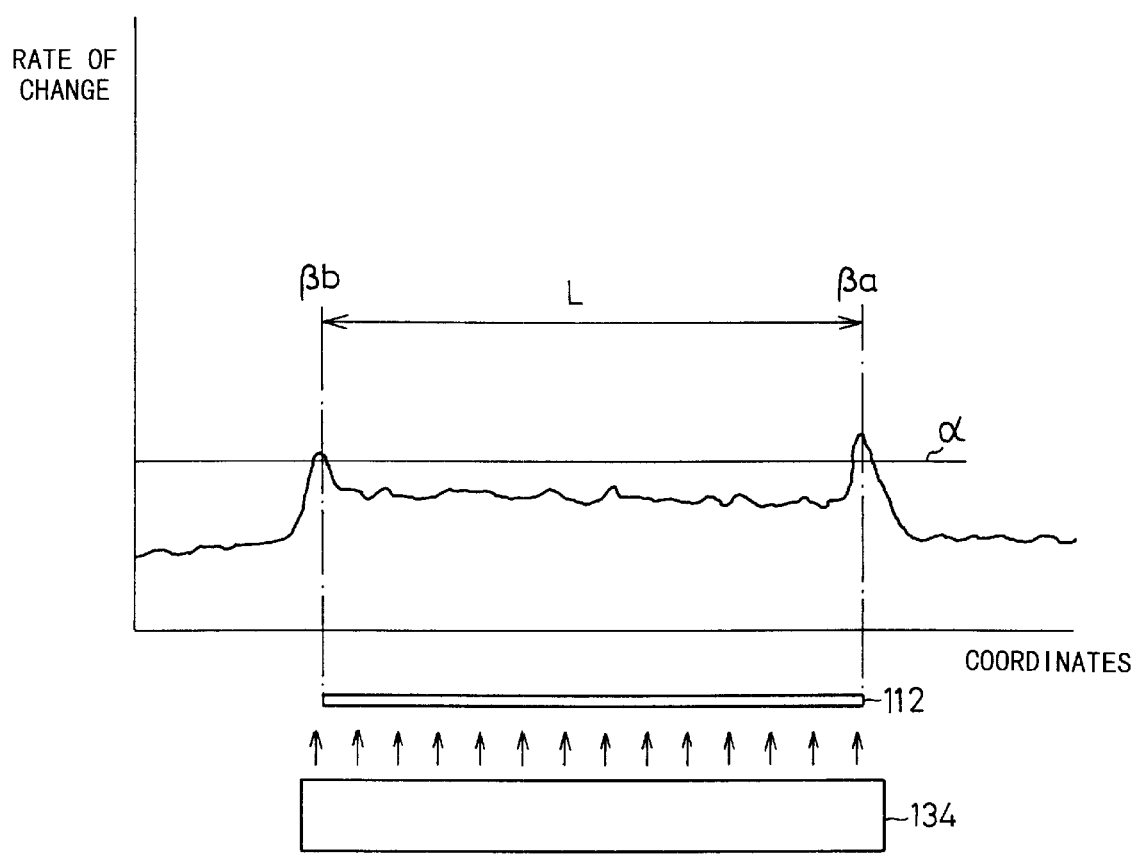
FIG. 14 is a diagram showing a binary conversion process that is carried out based on a rate of change of a luminance level.

For example, as shown in FIG. 14, rates of change of the luminance level are determined along the line tools 182, and coordinates at which the rate of change exceeds the threshold α are specified as coordinates βa, βb from the leading end.

From these coordinates βa, βb, there are detected coordinates where the leading and trailing ends of the sheet-like photosensitive member 112 are actually positioned, i.e., coordinates on the feed path of the sheet-like photosensitive member 112.

In step S22 (dimension acquiring means), a dimension of the sheet-like photosensitive member 112, in particular, a length (measured length) L thereof, is detected based on the actual coordinates of the leading and trailing ends of the sheet-like photosensitive member 112 which have been obtained in step S21.

In step S23 (skew detecting means), a skew angle θ of the sheet-like photosensitive member 112 is detected from the difference between the coordinates Da, βb obtained in step S21.

Figure 15:
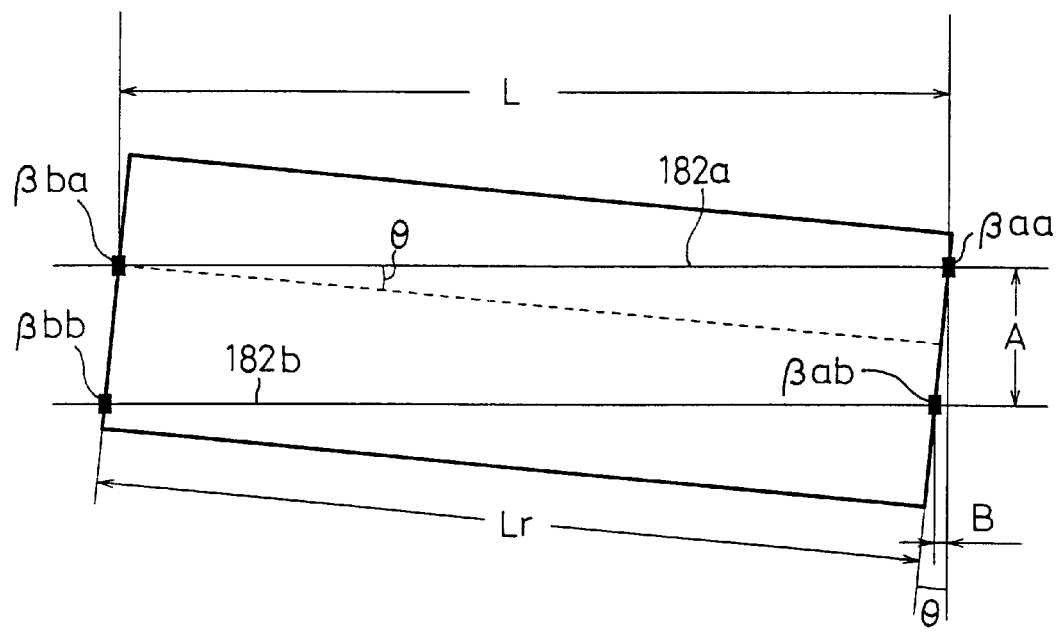
FIG. 15 is a diagram showing a process of determining a skew angle of a sheet member.

For example, as shown in FIG. 15, it is assumed that the distance between certain two line tools 182a, 182b is represented by A and the difference between the coordinates βa (referred to as coordinates βaa, βab) and the coordinates βb (referred to as coordinates βba, βbb) on the line tools 182a, 182b along the line tools 182a, 182b is represented by B. The skew angle θ of the sheet-like photosensitive member 112 is determined by θ=arctan(B/A).

In step S24 (skew correcting means), the measured length L obtained in step S22 is corrected based on the skew angle θ obtained in step S23, thus obtaining an actual length Lr of the sheet-like photosensitive member 112. The actual length Lr is determined as Lr=L×cosθ. If the skew angle θ is smaller than a predetermined value, then the processing in step S24 may be omitted.

In the third embodiment, the electronic flash lamp 134 applies infrared light in such a wavelength range which does not fog the sheet-like photosensitive member 112 to the sheet-like photosensitive member 112, and the infrared light is detected by the inlet CCD cameras 136a, 136b, 136c and the outlet CCD camera 138. Based on the detected infrared light, the positions of the ends of the sheet-like photosensitive member 112 are detected. Dimensions of the sheet-like photosensitive member 112 are then measured from the detected positions of the ends. Therefore, the sheet-like photosensitive member 112 is prevented from being fogged when dimensions of the sheet-like photosensitive member 112 are measured.

The threshold α used to perform the binary conversion process on the image data from the inlet CCD cameras 136a, 136b, 136c and the outlet CCD camera 138 is set depending on the infrared transmittance as an optical property of the sheet-like photosensitive member 112. Consequently, dimensions of various types of sheet-like photosensitive members having different transmittances can accurately be measured.

The skew angle θ of the sheet-like photosensitive member 112 is detected from the difference between the coordinates βa, βb corresponding to the ends of the sheet-like photosensitive member 112, which have been produced according to the binary conversion process, and the measured dimensional value of the sheet-like photosensitive member 112 is corrected based on the skew angle θ. Therefore, it is possible to reliably measure dimensions of the sheet-like photosensitive member 112 even when the sheet-like photosensitive member 112 is being fed in a skewed state.

Since the electronic flash lamp 134 emits infrared light for a given period of time only, dimensions of the sheet-like photosensitive member 112 can be measured while the sheet-like photosensitive member 112 is being fed. Thus, the period of time required to measure dimensions of the sheet-like photosensitive member 112 can be shortened. In addition, the sheet-like photosensitive member 112 is prevented from being fogged reliably.

When dimensions of the sheet-like photosensitive member 112 are measured, the sheet-like photosensitive member 112 is fed by being gripped by the belt conveyors 132a, 132b. Thus, the sheet-like photosensitive member 112 is prevented from being twisted or wound, and can accurately be measured for dimensions.

If the electronic flash lamp 134 is replaced with a matrix of infrared LEDs, then the light source can be constructed at a low cost.

Figure 16:
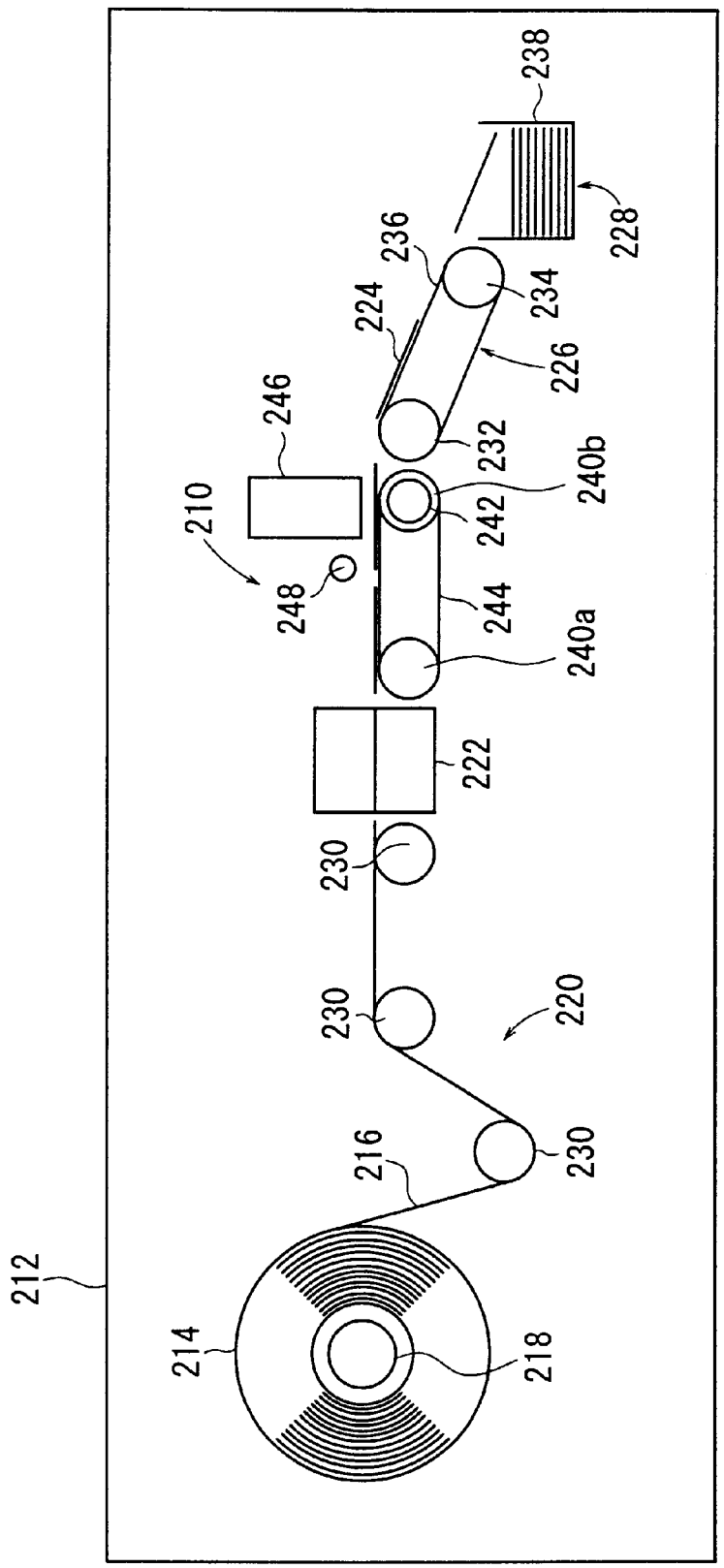
FIG. 16 is a schematic side elevational view of a sheet member manufacturing system which incorporates a marking apparatus according to a fourth embodiment of the present invention.

As shown in FIG. 16, a marking apparatus 210 according to a fourth embodiment of the present invention is incorporated in a sheet member manufacturing system 212. The sheet member manufacturing system 212 comprises a supply shaft 218 for unreeling a web 216 from a web roll 214, a first feeder 220 for feeding the web 216 from the supply shaft 218 to a cutter 222, a marking apparatus 210 for marking sheet-like webs 224 of given length successively cut form the web 216 by the cutter 222 with a latent image, and a second feeder 226 for feeding marked webs 224 to a stacking unit 228. The marked image may represent a manufacturing lot number representing manufacturing information such as a processed sequence and an ISO sensitivity value representing the sensitivity of a photosensitive member.

The supply shaft 218 is directly coupled to an actuator (not shown). When the actuator is energized, the supply shaft 218 is rotated about its own axis to unreel the web 216 from the web roll 214. The web 216 unreeled from the web roll 214 is fed by a plurality of feed rollers 330 of the first feeder 220 on a feed path of the web 216 to the cutter 222.

The cutter 222 has a blade (not shown) for cutting off the web 216 from the first feeder 220 into a sheet-like web 224 having a given length, which is typically an X-ray film. The sheet-like web 224 cut by the cutter 222 is marked with a manufacturing lot number and an ISO sensitivity value by the marking apparatus 210. Details of the marking apparatus 210 will be described later on.

The marked sheet-like web 224 is delivered onto a belt 236 trained around a pair of rollers 232, 234 of the second feeder 226. When the belt 236 is run in circulation by an actuator, not shown, the sheet-like web 224 is placed into a staking box 238 of the stacking unit 228.

Details of the marking apparatus 210 will be described below. As shown in FIG. 16, the marking apparatus 210 includes an exposure head 246, a drive roller 240a disposed below the exposure head 246, and a driven roller 240b disposed below the exposure head 246 and paired with the drive roller 240a. The driven roller 240b has a shaft to which a rotary encoder 242 is fixed. A feed belt 244 is trained around the drive roller 240a and the driven roller 240b. A photoelectric switch 248 is disposed near the exposure head 246.

Figure 17:
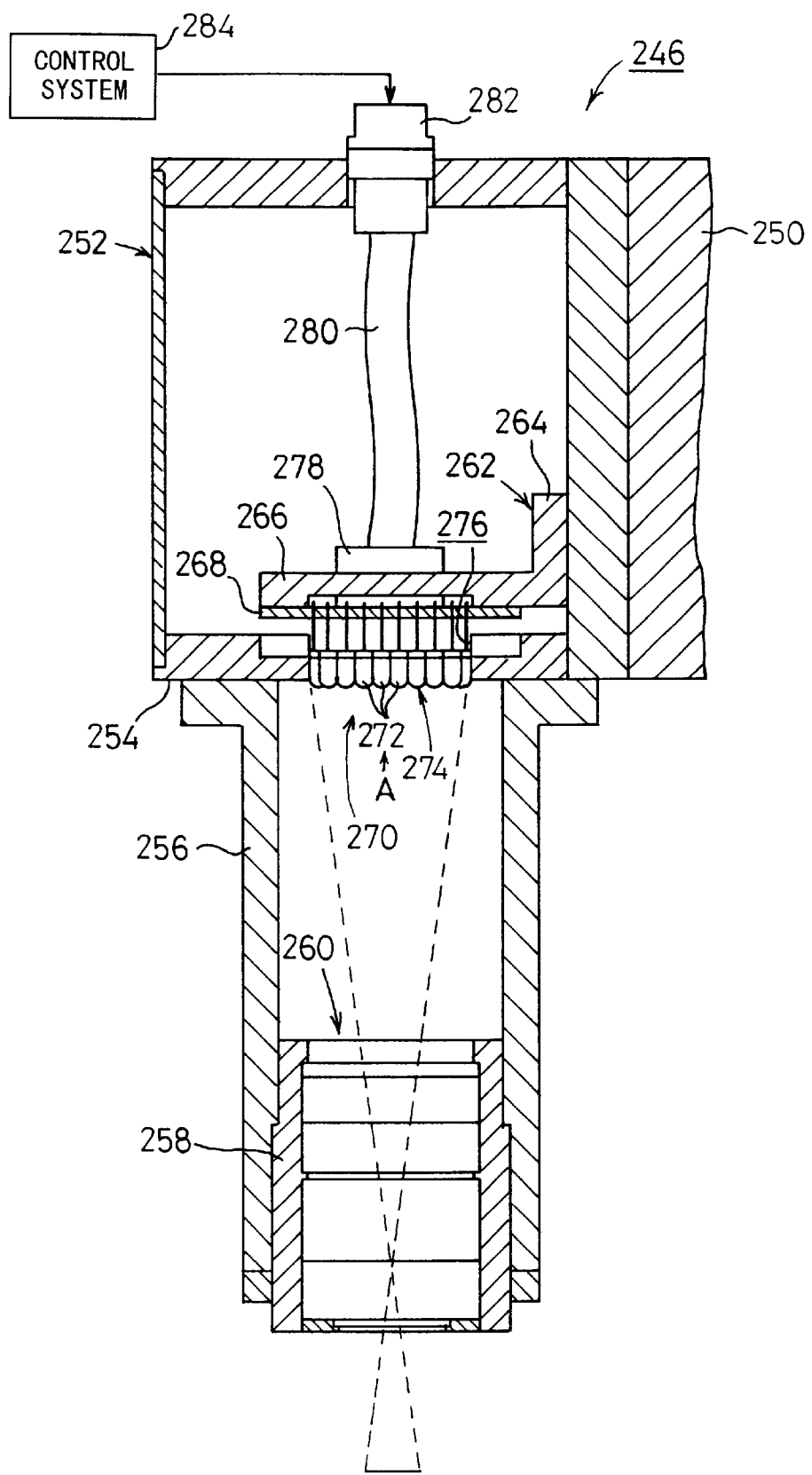
FIG. 17 is an enlarged vertical cross-sectional view of an exposure head of the marking apparatus shown in FIG. 16.
Figure 18:
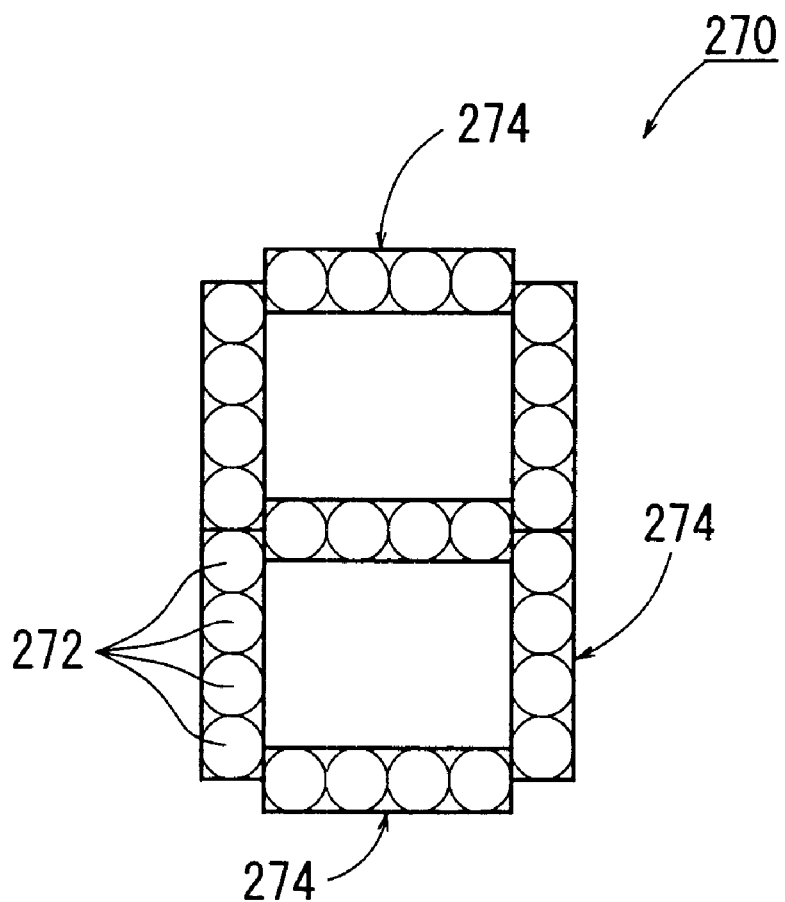
FIG. 18 is a view of a light source as viewed in the direction indicated by the arrow A in FIG. 17.

As shown in FIG. 17, the exposure head 246 comprises a casing 252 fixed to a support frame 250, and a tubular guide 256 extending downwardly from a bottom panel 254 of the casing 252 and fixed to the bottom panel 254. The guide 256 houses an optical system 260 that is supported in a tip end thereof by a holder 258. A mount base 262 has a bent wall 264 fixed to an inner wall surface of the casing 252, and a flat wall 266 extending substantially parallel to the bottom panel 254. A light source 270 comprising a plurality of white LEDs 272 is mounted on the flat wall 266 by a base plate 268. As shown in FIG. 18, the light source 270 includes a plurality of segments 274 made up of linear arrays of four LEDs 272, the segments 272 substantially representing a shape of numeral "8". The white LEDs 272 have tip ends projecting downwardly from an opening 276 defined in the bottom panel 254 of the casing 252. The optical system 260 and the light source 270 lie substantially parallel to the horizontal plane in FIG. 17.

A first socket 278 is fixed to an upper surface of the mount base 262, and connected by a lead wire 280 to a second socket 282 that is mounted in and extends substantially centrally through an upper panel of the casing 262. As shown in FIG. 17, the second socket 282 is connected to a control system 284.

Figure 19:
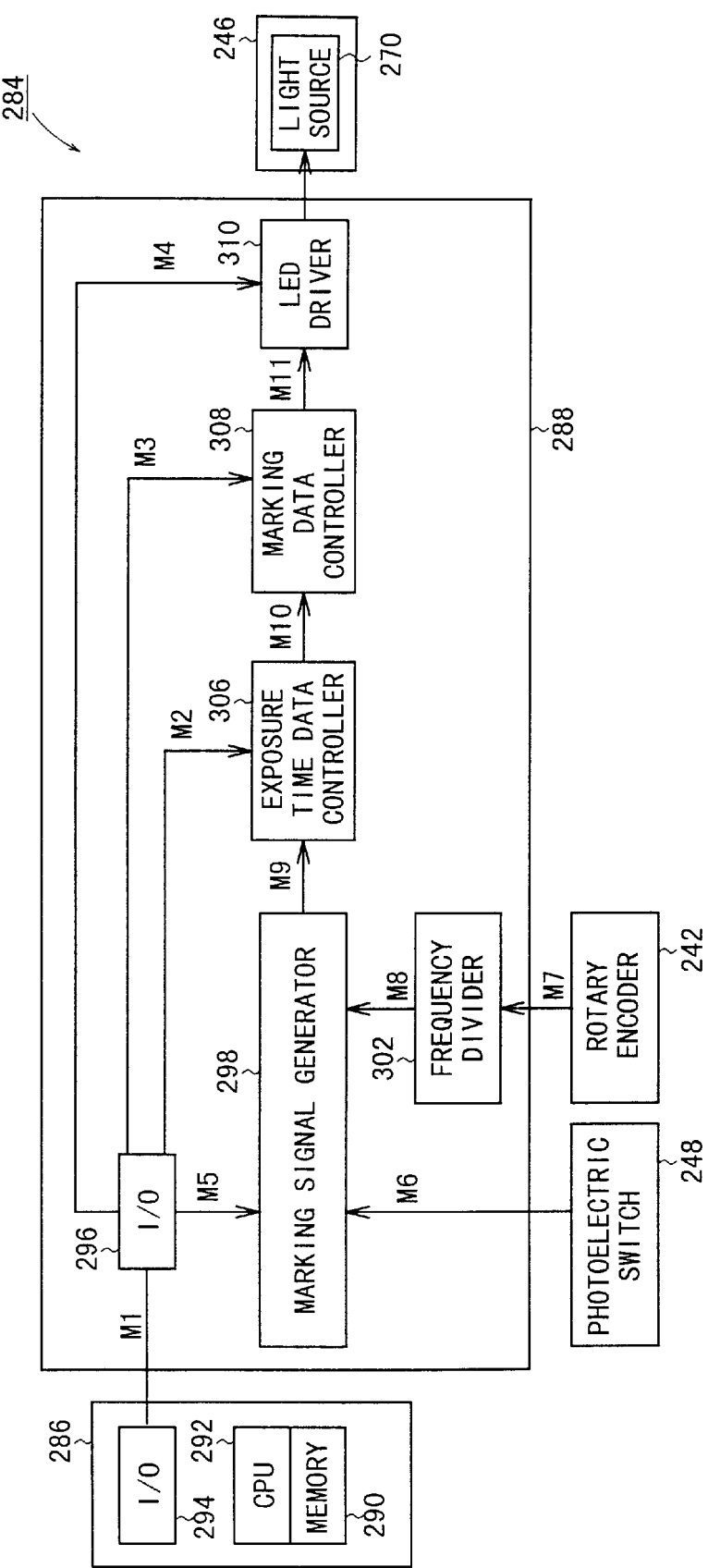
FIG. 19 is a block diagram of a controller of the marking apparatus shown in FIG. 16.

As shown in FIG. 19, the control system 284 has a controller 286 and a driver 288. The controller 286 comprises a memory (data storage unit) 290 for storing exposure time (time to energize the light source 270) data for a plurality of types of X-ray films having different photosensitive regions to be marked, marking data (representing characters to be marked), and current data (represents currents to be supplied to the light source 270), a CPU 292, and an input/output port 294. The input/output port 294 supplies a signal M1 representing the exposure time data, the marking data, and the current data to an I/O port 296 of the driver 288.

The driver 288 comprises a marking signal generator 298 for generating a marking start signal M9 to start marking the sheet-like web, a frequency divider 302 connected to the marking signal generator 298, an exposure time data controller 306 for storing exposure time data, a marking data controller 308 for storing marking data, and an LED driver (driving circuit) 310 for energizing the white LEDs 272 of the light source 270.

Figure 20:
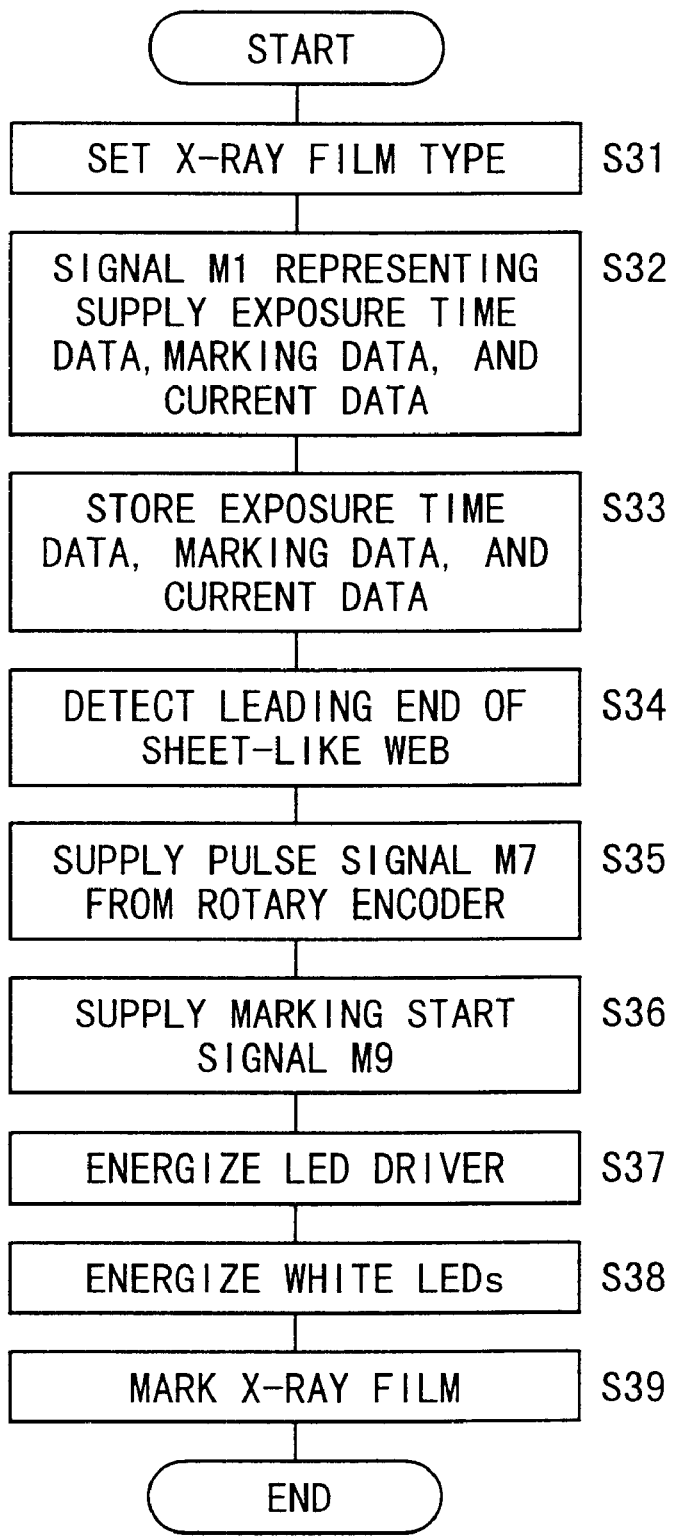
FIG. 20 is a flowchart of a marking sequence carried out by the marking apparatus shown in FIG. 16.

The sheet member manufacturing system 212 which incorporates the marking apparatus 210 is basically constructed as described above. Operation and advantages of the marking apparatus 210 will be described below with reference to FIG. 20.

The type of an X-ray film to be marked is set or selected among the types of a plurality of types of X-ray films having different photosensitive regions to be marked which are stored in the memory 290 in step S31. Since the memory 290 also stores exposure time dada, marking data, and current data corresponding to those types of X-ray films, an exposure time for the light source 270 for the X-ray film to be marked, characters to be marked, and a current to be supplied to the light source 270 are determined upon selection of the type of an X-ray film to be marked.

Figure 22:
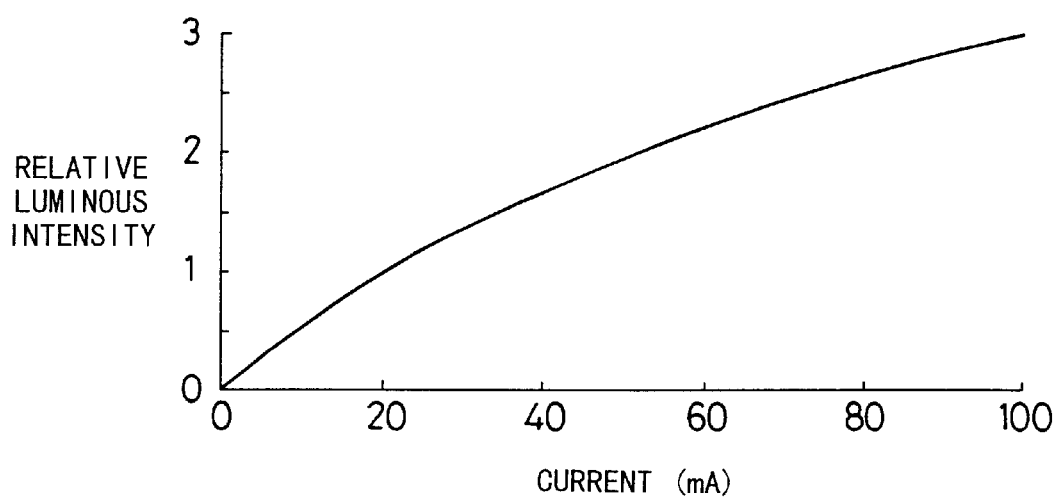
FIG. 22 is a graph showing the relationship between current values and relative luminous intensities.

The exposure time data and the current data stored in the memory 290 are such that, as shown in FIG. 21, if the X-ray film to be marked is of the type A, then the exposure time is 2 ps and the current is 20 mA, if the X-ray film to be marked is of the type B, then the exposure time is 10 ps and the current is 20 mA, if the X-ray film to be marked is of the type C, then the exposure time is 20 ps and the current is 20 mA, and if the X-ray film to be marked is of the type D, then the exposure time is 10 ps and the current is 100 mA. It has experimentally been confirmed that when the X-ray films of the types A through D are marked under the above conditions, a desired marking density (marked character density) is reliably maintained, without impairing the quality of marked characters. Furthermore, current values and relative luminous intensities are related to each other as shown in FIG. 22. Therefore, when the X-ray film of the type C is to be marked if only a current of 20 mA can be supplied, the exposure time may be set to 20 ps to achieve a desired marking density reliably.

Then, the CPU 292 of the controller 286 is operated to supply the signal M1 representing the exposure time data, the marking data, and the current data for the X-ray film to be marked from the input/output port 294 to the input/output port 296 of the driver 288. In the driver 288, a signal M2 representing the exposure time data is supplied from the input/output port 296 and stored in the exposure time data controller 306, and a signal M3 representing the marking data is supplied from the input/output port 296 and stored in the marking data controller 308 in step S33. A signal M4 representing the current data is supplied from the input/output port 296 and stored in the LED driver 310 also in step S33. At this time, the input/output port 296 supplies the marking signal generator 298 with a signal M5 representing that the exposure time data, the marking data, and the current data are stored respectively in the exposure time data controller 306, the marking data controller 308, and the LED driver 310.

During this time, the supply shaft 218 rotates to unreel the web 216, which is fed by the first feeder 220 to the cutter 222. The cutter 222 cuts off the web 216 into a sheet-like web 244 having a given length. The sheet-like web 244 is then delivered to a position below the photoelectric switch 248 by the feed belt 244 which is actuated by the drive roller 240a of the marking apparatus 210. The photoelectric switch 248 detects a leading end of the sheet-like web 244 in step S34. When the photoelectric switch 248 detects the leading end of the sheet-like web 244, it generates a detected signal M6, which is applied to the marking signal generator 298.

Immediately after the photoelectric switch 248 detects the leading end of the sheet-like web 244, the rotary encoder 242 generates a pulse signal M7 representing the angular displacement thereof and applies the pulse signal M7 to the frequency divider 302 in step S35. When the frequency of the pulse signal M7 is divided into a preset value by the frequency divider 302, the frequency divider 302 applies a control signal M8 to the marking signal generator 298. The marking signal generator 298 then applies a marking start signal M9 to the exposure time data controller 306 in step S36.

Subsequently, the exposure time data controller 306 applies a control signal M10 for controlling the exposure time to the marking data controller 308. Then, the marking data controller 308 applies a control signal M11, which corresponds to the signal M3 for the marking data and the control signal M10 for the exposure time, to the LED driver 310, thus energizing the LED driver 310 in step S37. Since the LED driver 310 has been supplied with the signal M4 representing the current data, the LED driver 310 energizes the white LEDs 272 to emit light with a given intensity for a given period of time in order to produce characters to be marked in step S38, thus marking desired characters on the sheet-like web 224 in step S39. Specifically, light emitted from the white LEDs 272 passes through the optical system 260, and reaches the sheet-like web 224 to make the characters as a latent image thereon.

The rotary encoder 242 applies the pulse signal M7 to the frequency divider 302 each time it rotates a certain angle. When the frequency of the pulse signal M7 is divided into a preset value by the frequency divider 302, the frequency divider 302 applies the control signal M8 to the marking signal generator 298. Thus, even after a first character is marked on the sheet-like web 224, desired characters are marked at a given character spacing until finally a manufacturing lot number and an ISO sensitivity value are marked on the sheet-like web 224.

The sheet-like web 224 marked with the manufacturing lot number and the ISO sensitivity value is then placed into the stacking box 238 of the stacking unit 228. After a certain number of marked sheet-like webs 224 are stacked in the stacking box 238, the stacking box 238 is delivered by a feed device, not shown, to a next process to process the sheet-like webs 224.

With the stacking apparatus according to the present invention, after a first sheet member to be stacked is temporarily held above the stacking position by the sheet member holding means, the sheet member holding means is moved to drop the sheet member into the stacking position. Thus, the sheet member can smoothly and highly accurately be placed desirably in the stacking position. Since the sheet member is prevented from impinging upon the stacking bottom plate and the lining cardboard in the stacking position, the sheet member is free from a stacking failure and a quality failure due to damage, and the process of stacking sheet members is made efficient with ease.

In the dimension measuring apparatus according to the present invention, dimensions of sheet members are measured by using infrared light. Therefore, the sheet members are reliably prevented from being fogged.

According to the present invention, furthermore, sheet members having various different photosensitive regions can be marked with desired characters by LEDs of one color, and the LEDs are energized by one LED driver. Therefore, the marking apparatus with such LEDs can be small in size. Consequently, the cost of the marking apparatus can be reduced, and the marking apparatus can easily be maintained and managed.

Although certain preferred embodiments of the present invention have been shown and described in detail, it should be understood that various changes and modifications may be made therein without departing from the scope of the appended claims.

What is claimed is:

1. An apparatus for stacking a predetermined number of sheet-like photosensitive members successively conveyed by a feed system in a stacking position, comprising:

sheet-like photosensitive member holding means disposed above said stacking position for temporarily holding at least a first sheet-like photosensitive member that is conveyed; and actuating means for displacing said holding means from above said stacking position to drop said sheet-like photosensitive member held by said holding means into said stacking position.

2. An apparatus according to claim 1, further comprising:

variable stopper means for engaging and releasing the sheet-like photosensitive member from said holding means when said holding means is moved away from said stacking position.

3. An apparatus according to claim 2, wherein said variable stopper means comprises:

a pulling guide angularly movable by an actuator;

said pulling guide having a guide bent toward said sheet-like photosensitive member held by said holding means for engagement with said sheet-like photosensitive member.

4. An apparatus according to claim 1, further comprising:

a sheet-like photosensitive member sensor for detecting when said first sheet-like photosensitive member is held by said holding means.

5. An apparatus for stacking a predetermined number of sheet-like photosensitive members successively conveyed by a feed system in a stacking position, comprising:

sheet-like photosensitive member holder disposed above said stacking position for holding temporarily at least a first sheet-like photosensitive member that is conveyed;

actuator means for displacing said holder from above said stacking position to drop said sheet-like photosensitive member held by said holder into said stacking position, wherein said holder comprises:
   a plurality of temporary receiver rods substantially stationary with respect to each other, extending in the direction in which said sheet-like photosensitive member is conveyed, each of said temporary receiver rods having a plurality of air ejection holes which are open toward said sheet-like photosensitive member.

6. An apparatus for stacking a predetermined number of sheet-like photosensitive members successively conveyed by a feed system in a stacking position, comprising:

sheet-like photosensitive member holding means disposed above said stacking position for holding temporarily at least a first sheet-like photosensitive member that is conveyed;

actuator means for displacing said holding means from above said stacking position to drop said sheet-like photosensitive member held by said holding means into said stacking position, wherein said holding means comprises:
   a plurality of temporary receiver rods extending in the direction in which said sheet-like photosensitive member is conveyed, each of said temporary receiver rods having a plurality of air ejection holes which are open toward said sheet-like photosensitive member, wherein said temporary receiver rods have respective plates with said air ejection holes defined therein, said plates having respective surfaces treated to provide a reduced coefficient of a friction.

7. An apparatus according to claim 6, wherein each of said plates has round edges on opposite sides and distal ends thereof.

8. A photosensitive sheet member stacking apparatus to stack a predetermined number of photosensitive sheet members in a stacking position, comprising:

a photosensitive sheet member holder disposed above said stacking position and configured to hold temporarily at least a first photosensitive sheet member of said predetermined number of photosensitive sheet members, the holder comprising a plurality of receiver rods substantially stationary with respect to each other, the rods extending in the direction in which said first member is conveyed, each of said receiver rods having a plurality of air holes open toward said first member and having surfaces treated to provide a reduced coefficient of friction; and an actuator configured to displace said holder from above said stacking position to drop said first member held by said holder into said stacking position.

9. The stacking apparatus of claim 8, wherein each of the rods has round edges on opposite sides and distal ends thereof.

* * * * *